(12) United States Patent
Okamoto et al.

(10) Patent No.: US 8,354,497 B2
(45) Date of Patent: Jan. 15, 2013

(54) PEPTIDE BINDING TO METHYLATED DNA

(75) Inventors: Akimitsu Okamoto, Saitama (JP); Akiko Nomura, Saitama (JP)

(73) Assignee: Riken, Wako-shi, Saitama (JP)

( * ) Notice: Subject to any disclaimer, the term of this patent is extended or adjusted under 35 U.S.C. 154(b) by 0 days.

(21) Appl. No.: 13/502,272

(22) PCT Filed: Oct. 15, 2010

(86) PCT No.: PCT/JP2010/068194
§ 371 (c)(1), (2), (4) Date: May 30, 2012

(87) PCT Pub. No.: WO2011/046214
PCT Pub. Date: Apr. 21, 2011

(65) Prior Publication Data
US 2012/0238038 A1 Sep. 20, 2012

(30) Foreign Application Priority Data
Oct. 16, 2009 (JP) ................................. 2009-239657

(51) Int. Cl.
*C07K 14/00* (2006.01)
(52) U.S. Cl. ......... 530/300; 530/304; 530/324; 530/326
(58) Field of Classification Search .................. None
See application file for complete search history.

(56) References Cited

U.S. PATENT DOCUMENTS

| | | | |
|---|---|---|---|
| 6,977,154 B1 * | 12/2005 | Choo et al. | 435/7.1 |
| 7,425,415 B2 | 9/2008 | Pfeifer et al. | |
| 2008/0260743 A1 | 10/2008 | Rehli | |
| 2009/0130659 A1 | 5/2009 | Rehli | |

FOREIGN PATENT DOCUMENTS

| | | |
|---|---|---|
| JP | 2002-506640 A | 3/2002 |
| JP | 2008-521388 A | 6/2008 |
| JP | 2008-521389 A | 6/2008 |
| WO | WO 99/47656 A2 | 9/1999 |
| WO | WO 2006/056478 A1 | 6/2006 |
| WO | WO 2006/056480 A2 | 6/2006 |

OTHER PUBLICATIONS

UniProtKB/TrEMBL Protein Accession No. C4PGM0 at http://www.uniprot.org/uniprot/C4PGM0, accessed Sep. 26, 2012.*
Butkus et al., *Nucleic Acids Research*, 15(17): 7091-7102 (1987).
Clark et al., *Nucleic Acids Research*, 22(15): 2990-2997 (1994).
Frommer et al., *Proc. Natl. Acad. Sci. USA*, 89: 1827-1831 (1992).
Gonzalgo et al., *Nucleic Acids Research*, 25(12): 2529-2531 (1997).
Hayatsu et al., *Biochemistry*, 9(14): 2858-2865 (1970).
Herman et al., *Proc. Natl. Acad. Sci. U.S.A.*, 93: 9821-9826 (1996).
Jacinto et al., *Biotechniques*, 44(1): 35-43 (2008).
Kane et al., *Cancer Research*, 57: 808-811 (1997).
Liu et al., *BMC Genomics*, 4: 19 (May 9, 2003).
Nelson et al., *Nucleic Acids Research*, 21(3): 681-686 (1993).
Ng et al., *Current Opinion in Genetics & Development*, 9: 158-163 (1999).
Okamoto, Akimitsu, *Bull. Chem. Soc. Jpn.*, 78: 2083-2097 (2005).
Okamoto et al., *J. Am. Chem. Soc.*, 124: 10262-10263 (2002).
Okamoto et al., *Org. Biomol. Chem.*, 4: 1638-1640 (2006).
Okamoto, Akimitsu, *Organic & Biomolecular Chemistry*, 7(1): 21-26 (2009).
Pfaffl, Michael, *Nucleic Acids Research*, 29(9): e45 (2001).
Reynaud et al., *Cancer Letters*, 61: 255-262 (1991).
Tanaka et al., *Bioorganic & Medicinal Chemistry*, 15: 1615-1621 (2007).
Tanaka et al., *J. Am. Chem. Soc.*, 127: 5612-5620 (2007).
Tanaka et al., *J. Am. Chem. Soc.*, 129: 14511-14517 (2007).
Tasseron-De Jong, *Gene*, 74: 147-149 (1988).
Warnecke et al., *Methods*, 27: 101-107 (2002).
Weber et al., *Nature Genetics*, 37(8): 853-862 (2005).
Weber et al., *Nature Genetics*, 39(4): 457-466 (2007).
Zilberman et al., *Nature Genetics*, 39(1): 61-69 (2007).
Japanese Patent Office, International Search Report in International Patent Application No. PCT/JP2010/068194 (Jan. 18, 2011) English translation.
Japanese Patent Office, Written Opinion in International Patent Application No. PCT/JP2010/068194 (Jan. 18, 2011) English translation.
Butkus et al., "Cleavage of methylated CCCGGG sequences containing either N4-methylcytosine or 5-methylcytosine with MspI, HpaII, SmaI, XmaI and Cfr9I restriction endonucleases," *Nucleic Acids Research*, 15(17): 7091-7102 (1987).
Clark et al., "High sensitivity mapping of methylated cytosines," *Nucleic Acids Research*, 22(15): 2990-2997 (1994).
Frommer et al., "A genomic sequencing protocol that yields a positive display of 5-methylcytosine residues in individual DNA strands," *Proc. Natl. Acad. Sci. USA*, 89: 1827-1831 (1992).
Gonzalgo et al., "Rapid quantitation of methylation differences at specific sites using methylation-sensitive single nucleotide primer extension (Ms-SNuPE)," *Nucleic Acids Research*, 25(12): 2529-2531 (1997).
Hayatsu et al., "Reaction of sodium bisulfite with uracil, cytosine, and their derivatives," *Biochemistry*, 9(14): 2858-2865 (1970).
Herman et al., "Methylation-specific PCR: a novel PCR assay for methylation status of CpG islands," *Proc. Natl. Acad. Sci. U.S.A.*, 93: 9821-9826 (1996).
Jacinto et al., "Methyl-DNA immunoprecipitation (MeDIP): Hunting down the DNA methylome," *Biotechniques*, 44(1): 35-43 (2008).
Kane et al., "Methylation of the *hMLH1* promoter correlates with lack of expression of hMLH1 in sporadic colon tumors and mismatch repair-defective human tumor cell lines," *Cancer Research*, 57: 808-811 (1997).

(Continued)

*Primary Examiner* — Christina Bradley
*Assistant Examiner* — Kristina M Hellman
(74) *Attorney, Agent, or Firm* — Leydig, Voit & Mayer, Ltd.

(57) ABSTRACT

The present invention aims to provide a tool etc. capable of detecting a methylated region of a DNA in a short time, in a labor-saving manner and without being limited by nucleotide sequences, and further capable of quantifying the methylation. The present invention provides a peptide containing a metal finger motif and a tyrosine derivative in a helix forming part of the motif, which recognizes and binds to a methylated region of a double stranded DNA.

6 Claims, 3 Drawing Sheets

OTHER PUBLICATIONS

Liu et al., "Development and validation of a T7 based linear amplification for genomic DNA," *BMC Genomics*, 4: 19 (May 9, 2003).

Nelson et al., "Restriction endonuclease cleavage of 5-methyl-deoxycytosine hernimethylated DNA at high enzyme-to-substrate ratios," *Nucleic Acids Research*, 21(3): 681-686 (1993).

Ng et al., "DNA methylation and chromatin modification," *Current Opinion in Genetics & Development*, 9: 158-163 (1999).

Okamoto, Akimitsu, "Synthesis of highly functional nucleic acids and their application to DNA technology," *Bull. Chem. Soc. Jpn.*, 78: 2083-2097 (2005).

Okamoto et al., "Site-specific discrimination of cytosine and 5-methylcytosine in duplex DNA by peptide nucleic acids," *J. Am. Chem. Soc.*, 124: 10262-10263 (2002).

Okamoto et al., "Sequence-selective osmium oxidation of DNA: efficient distinction between 5-methylcytosine and cytosine," *Org. Biomol. Chem.*, 4: 1638-1640 (2006).

Okamoto, Akimitsu, "Chemical approach toward efficient DNA methylation analysis," *Organic & Biomolecular Chemistry*, 7(1): 21-26 (2009).

Pfaffl, Michael, "A new mathematical model for relative quantification in real-time RT-PCR," *Nucleic Acids Research*, 29(9): e45 (2001).

Reynaud et al., "Monitoring of urinary excretion of modified nucleosides in cancer patients using a set of six monoclonal antibodies," *Cancer Letters*, 61: 255-262 (1991).

Tanaka et al., "Methylcytosine-selective fluorescence quenching by osmium complexation," *Bioorganic & Medicinal Chemistry*, 15: 1615-1621 (2007).

Tanaka et al., "Direct labeling of 5-methylcytosine and its applications," *J. Am. Chem. Soc.*, 127: 5612-5620 (2007).

Tanaka et al., "An osmium-DNA interstrand complex: application to facile DNA methylation analysis," *J. Am. Chem. Soc.*, 129: 14511-14517 (2007).

Tasseron-De Jong et al., "The ability of the restriction endonuclease *Eco*RI to digest hemi-methylated versus fully cytosine-methylated DNA of the herpes *tk* promoter region," *Gene*, 74: 147-149 (1988).

Warnecke et al., "Identification and resolution of artifacts in bisulfite sequencing," *Methods*, 27: 101-107 (2002).

Weber et al., "Chromosome-wide and promoter-specific analyses identify sites of differential DNA methylation in normal and transformed human cells," *Nature Genetics*, 37(8): 853-862 (2005).

Weber et al., "Distribution, silencing potential and evolutionary impact of promoter DNA methylation in the human genome," *Nature Genetics*, 39(4): 457-466 (2007).

Zilberman et al., "Genome-wide analysis of *Arabidopsis thaliana* DNA methylation uncovers an interdependence between methylation and transcription," *Nature Genetics*, 39(1): 61-69 (2007).

Japanese Patent Office, International Search Report in International Patent Application No. PCT/JP2010/068194 (Jan. 18, 2011), English translation.

Japanese Patent Office, Written Opinion in International Patent Application No. PCT/JP2010/068194 (Jan. 18, 2011), English translation.

\* cited by examiner (A)

(B)

(C)

(D)

target DNA

GMG (methylated)

5'- GGGGMGGGGCC -3'
3'- CCCCGMCCCGG -5'

GCG (unmethylated)

5'- GGGGCGGGGCC -3'
3'- CCCCGCCCCGG -5'

(1) peptide Y

GMG

GCG (2) peptide Y(PO3)

GMG

GCG (3) peptide F

GMG

GCG (4) peptide Y(SO3)

GMG

GCG

PEPTIDE BINDING TO METHYLATED DNA

CROSS-REFERENCE TO RELATED APPLICATION(S)

The present application is the U.S. national phase of International Patent Application PCT/JP2010/068194, filed on Oct. 15, 2010, which claims priority to Japanese Patent Application 2009-239657, filed on Oct. 16, 2009.

INCORPORATION-BY-REFERENCE OF MATERIAL ELECTRONICALLY SUBMITTED

Incorporated by reference in its entirety herein is a computer-readable nucleotide/amino acid sequence listing submitted concurrently herewith and identified as follows: 5,876 bytes ASCII (Text) file named "710188ReplacementsSequenceListing" created Sep. 25, 2012.

TECHNICAL FIELD

The present invention relates to a methylated DNA-binding peptide, and more particularly, to a peptide that recognizes and binds to a methylated region of a double stranded DNA. In addition, the present invention relates to a kit comprising the peptide and a method of detecting a methylated region of a double stranded DNA, comprising using the peptide.

BACKGROUND ART

Epigenetics is the discipline where information inherited or succeeded to after cell division is handled without being based on the base sequences of genes. This information is maintained by DNA methylation and histone modifications. DNA methylation or histone modifications mainly control gene switching, i.e., whether or not genes work. For this reason, cells and individuals, even with exactly the same gene base sequences, can have totally different phenotypes.

DNA methylation occurs mainly as the methylation of the 5-position carbon in the cytosine residue; for example, in higher eukaryotes, the cytosine present in the CpG sequence (a sequence with cytosine (C) followed by guanine (G), from the 5' side, in the 5'-CG-3' arrangement on the base sequence of DNA) is known to be methylated. The CpG sequence is also present in promoter regions of many genes; it is generally said that the methylation of the cytosine in the CpG sequence in the promoter region suppresses gene transcription. For this reason, it is thought that the methylation of the cytosine in the CpG sequence represents an important epigenetic mechanism involved in the regulation of gene expression in higher eukaryotes, and plays an important role in the cellular functions themselves.

Epigenetics is involved in a wide variety of life phenomena such as development, differentiation, genome imprinting, and X chromosome inactivation. Also, in diseases, methylation abnormalities in cancer are well known; it has recently been suggested that methylation abnormalities are also involved in a wide variety of non-cancer diseases such as schizophrenia and diabetes. Also, it has been increasingly evident that the methylation is instable in vitro; it is thought that it will become important in regenerative medicine to determine whether the methylation state of organs differentiation-induced from stem cells is normal.

While 60 to 90% of cytosine residues in the CpG sequence are methylated in mammals, the cytosine in the CpG sequence (CpG island), which is densely present in promoter regions of genes, is often not methylated (non-patent document 1). However, if an unmethylated region is methylated by a certain cause, gene transcription will be suppressed. For example, if the transcription of a cancer suppressor gene in cancer cells is inactivated, the growth of the cancer cells will become uncontrollable. Conversely, if the CpG island, which is normally methylated, fails to be methylated due to a certain abnormality, gene inactivation (stability) cannot be maintained, which in turn not only prevents the cells from exhibiting their essential functions, but also can produce functional abnormalities such as cell and tissue differentiation abnormalities. Therefore, the presence or absence of methylation and changes in the pattern thereof can provoke diseases such as cancer and differentiation abnormalities; examining the methylation pattern is strongly demanded also for the sake of treatment and prevention of such diseases.

To detect methylated DNA, a wide variety of methods have traditionally been attempted; for example, a method using a methylation-sensitive restriction endonuclease is known (non-patent documents 2 to 7). A methylation-sensitive restriction endonuclease is an enzyme that is unable to cleave DNA when the recognition site is methylated; although this method is effective in detecting methylation, the CpG site to be analyzed need to be a recognition sequence for the methylation-sensitive restriction endonuclease, so that the degree of freedom of the analysis is low, and a pretreatment for DNA purification is needed. Also, an analytical time of several hours or more to detection is required, including enzymatic reaction time.

Against this background, as methods of detection not relying on nucleotide sequences, methods wherein unmethylated cytosine is reacted with a hydrogen sulfite salt to convert it to uracil, and this is followed by PCR and sequencing (non-patent documents 8 to 13), immunoprecipitation methods using an anti-methylated cytosine antibody have been developed (patent document 1, non-patent documents 14 to 20). However, these methods also necessitate pretreatments such as alkali treatment and fragmentation; a long detection time of 5 to 16 hours is taken, with no improvement achieved in detectability at high sensitivity. In contrast, methods of specifically detecting methylated cytosine by allowing a combination of bipyridine-modified DNA and osmium oxide to selectively form a complex with methylated cytosine have been developed (non-patent documents 21 to 25), enabling the detection at higher sensitivity thanks to signal intensification, but the drawback of necessity for pretreatments such as heating after complex formation could not be resolved. Also, attempts have been made for methods utilizing methylated DNA-binding protein (MBP) (patent documents 2 and 3), but the molecular weight of MBP itself is extremely high at several tens of thousands to several hundreds of thousands, and there is still room for improvements in terms of stable supply, storage stability, or the ease of handling.

DOCUMENT LIST

Patent Documents patent document 1: U.S. Pat. No. 7,425,415
patent document 2: JP-A-2008-521388
patent document 3: JP-A-2008-521389

Non-Patent Documents non-patent document 1: Ng H H et al., Curr Opin Genet Dev. 1999, 9, 158-163.

non-patent document 2: Kane M F et al., Cancer Res. 1997, 57, 808-811.
non-patent document 3: Okamoto A et al., J Am Chem. Soc. 2002, 124, 10262-10263.
non-patent document 4: Okamoto A., Bull Chem Soc Jpn. 2005, 78, 2083-2097.
non-patent document 5: Nelson P S et al., Nucleic Acids Res. 1993, 21, 681-686.
non-patent document 6: Tasseron-de Jong J G et al., Gene. 1988, 74, 147-149.
non-patent document 7: Butkus V et al., Nucleic Acids Res. 1987, 15, 7091-7102.
non-patent document 8: Hayatsu H et al., Biochemistry. 1970, 9, 2858-2865.
non-patent document 9: Gonzalgo M L et al., Nucleic Acids Res. 1997; 25, 2529-2531.
non-patent document 10: Herman J G et al., Proc Natl Acad Sci USA. 1996, 93, 9821-9826.
non-patent document 11: Clark S J et al., Nucleic Acids Res. 1994, 22, 2990-2997.
non-patent document 12: Frommer M et al., Proc Natl Acad Sci USA. 1992, 89, 1827-1831.
non-patent document 13: Warnecke P M et al., Methods. 2002, 27, 101-107.
non-patent document 14: Pfaffl M W., Nucleic Acids Res. 2001, 29(9):e45.
non-patent document 15: Liu C L et al., BMC Genomics. 2003, 4, 1-11.
non-patent document 16: Weber M at al., Nat. Genet. 2005, 37, 853-862.
non-patent document 17: Weber M et al., Nat. Genet. 2007, 39, 457-466.
non-patent document 18: Zilberman D et al., Nat. Genet. 2007, 39, 61-69.
non-patent document 19: Reynaud C at al., Cancer Lett. 1992, 61, 255-262.
non-patent document 20: Jacinto F V et al., Biotechniques. 2008, 44, 35-43.
non-patent document 21: Okamoto A et al., Org Biomol Chem. 2006, 4, 1638-1640.
non-patent document 22: Tanaka K et al., Bioorg Med. Chem. 2007, 15, 1615-1621.
non-patent document 23: Tanaka K et al., J Am Chem. Soc. 2007, 129, 5612-5620.
non-patent document 24: Tanaka K et al., J Am Chem. Soc. 2007, 129, 14511-14517.
non-patent document 25: Okamoto A., Org Biomol Chem. 2009, 7, 21-26.

SUMMARY OF THE INVENTION

Problems to be Solved by the Invention

The present invention has been made in view of the above-mentioned problems, and the problem to be solved by the invention is to provide a tool capable of detecting a methylated region of a DNA in a short time, in a labor-saving manner and without being limited by nucleotide sequences, and further capable of quantifying the methylation.

Means of Solving the Problems

The present inventors have conducted intensive studies in an attempt to solve the above-mentioned problem and found that affinity for polynucleotide (DNA) containing methylated cytosine is improved by using a peptide having a metal finger motif introduced with a tyrosine derivative into a helix forming part of the motif. The present inventors have conducted further studies and successfully utilized the peptide not only for the detection of methylated cytosine but also quantification thereof, which resulted in the completion of the present invention.

Accordingly, the present invention provides the following.

(1) A peptide comprising a metal finger motif and a tyrosine is derivative in a helix forming part of the motif, which recognizes and binds to a methylated region of a double stranded DNA.

(2) The peptide of (1), wherein the aforementioned metal is selected from the group consisting of zinc, cobalt, iron, cadmium, magnesium, manganese and calcium.

(3) The peptide of (1) or (2), wherein the metal finger motif comprises a structure represented by the following formula (I):

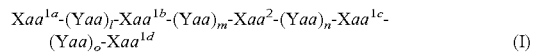

$$Xaa^{1a}\text{-}(Yaa)_l\text{-}Xaa^{1b}\text{-}(Yaa)_m\text{-}Xaa^{2}\text{-}(Yaa)_n\text{-}Xaa^{1c}\text{-}(Yaa)_o\text{-}Xaa^{1d} \quad (I)$$

wherein $Xaa^{1a}$, $Xaa^{1b}$, $Xaa^{1c}$ and $Xaa^{1d}$ are the same or different and each is cysteine or histidine, $Xaa^2$ is tyrosine or a derivative thereof, Yaa is any amino acid, l is an integer of 2 or 4, m is an integer of 6-10, n is an integer of 2-4, and o is an integer of 3-5.

(4) The peptide of (3), wherein (Yaa)$_m$ in the aforementioned formula (I) is a structure represented by the following formula (II):

$$(Yaa)_{m1}\text{-}Xaa^{3a}\text{-}(Yaa)_{m2} \quad (II)$$

wherein $Xaa^{3a}$ is phenylalanine, tyrosine or leucine, Yaa is any amino acid, m1 is an integer of 2-4, and m2 is an integer of 3-5.

(5) The peptide of (3) or (4), wherein (Yaa)$_n$ in the aforementioned formula (I) is a structure represented by the following formula (III):

$$Xaa^{3b}\text{-}(Yaa)_{n1} \quad (III)$$

wherein $Xaa^{3b}$ is phenylalanine, tyrosine or leucine, Yaa is any amino acid, and n1 is an integer of 1-3.

(6) The peptide of (4) or (5), wherein (Yaa)$_{m1}$ in the aforementioned formula (II) is a structure represented by the following formula (IV):

$$(Yaa)_{m3}\text{-}Xaa^{4a}\text{-}(Yaa)_{m4} \quad (IV)$$

wherein $Xaa^{4a}$ is lysine, arginine or histidine, Yaa is any amino acid, and m3 and m4 are each an integer of 0-2.

(7) The peptide of (5) or (6), wherein (Yaa)$_{n1}$ in the aforementioned formula (III) is a structure represented by the following formula (V):

$$(Yaa)_{n2}\text{-}Xaa^{4b} \quad (V)$$

wherein $Xaa^{4b}$ is lysine, arginine or histidine, Yaa is any amino acid, and n2 is an integer of 0-2.

(8) The peptide of any of (4)-(7), wherein (Yaa)$_{m2}$ in the aforementioned formula (II) is a structure represented by the following formula (VI):

$$(Yaa)_{m5}\text{-}Xaa^{4c}\text{-}(Yaa)_{m6} \quad (VI)$$

wherein $Xaa^{4c}$ is arginine, Yaa is any amino acid, m5 is an integer of 0-2, and m6 is an integer of 1-3.

(9) The peptide of any of (1)-(8), wherein the tyrosine derivative is a compound represented by the following formula (VII):

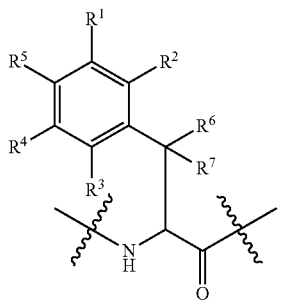

(VII)

wherein
R¹, R², R³, R⁴ and R⁵ are each independently a hydrogen atom, a halogen atom, an alkyl group, an alkoxy group, a nitro group, an amino group or a phosphorus-containing group, when R¹ and R², as well as R³ and R⁴, are not phosphorus-containing groups, they may be respectively joined to form an aromatic ring or an aromatic heterocycle, and
at least one of R¹, R², R³, R⁴ and R⁵ is a phosphorus-containing group, and
R⁶ and R⁷ are each independently a hydrogen atom, a halogen atom, an alkyl group, an alkoxy group, a nitro group, an amino group or a phosphorus-containing group.
(10) The peptide of any of (1)-(9), wherein the metal ion is coordinately bound.
(11) The peptide of (10), wherein the metal ion is selected from the group consisting of zinc ion, magnesium ion, cadmium ion, manganese ion, calcium ion, cobalt ion and iron ion.
(12) A kit for detection of a methylated region of a double stranded DNA, comprising the peptide of any of (1)-(9) and a metal ion supply compound.
(13) The kit of (12), wherein the metal ion supply compound is a compound comprising one or more metal atoms selected from the group consisting of zinc, magnesium, cadmium, manganese, calcium, cobalt and iron.
(14) A method of detecting a methylated region of a double stranded DNA, comprising the following steps (a) or (b), and (c):
(a) a step of contacting the peptide of any of (1)-(9), a metal ion supply compound and a double stranded DNA,
(b) a step of contacting the peptide of (10) or (11) and a double stranded DNA,
(c) a step of detecting the peptide bound to the methylated region of the aforementioned double stranded DNA.
(15) The detection method of (14), wherein the metal ion supply compound is a compound comprising one or more metal atoms selected from the group consisting of zinc, magnesium, cadmium, manganese, calcium, cobalt and iron.
(16) A method of inspecting DNA methylation abnormality in an obtained sample, comprising the following steps (i)-(iii):
(i) a step of contacting a sample obtained from a subject animal, the peptide of any of (1)-(9) and a metal ion supply compound, or the peptide of (10) or (11),
(ii) a step of measuring the peptide bound to a methylated region of a double stranded DNA contained in the aforementioned sample, and
(iii) a step of examining the presence or absence of DNA methylation abnormality by comparing the measurement results obtained for the subject animal in step (ii) with those of a normal control.
(17) The inspection method of (16), wherein the metal ion supply compound is a compound comprising one or more metal atoms selected from the group consisting of zinc, magnesium, cadmium, manganese, calcium, cobalt and iron.
(18) The inspection method of (16) or (17), wherein the DNA methylation abnormality is caused by a disease related to DNA methylation abnormality.
(19) The inspection method of (18), wherein the disease related to DNA methylation abnormality is cancer, a mental disease, a lifestyle-related disease, a neurological disease, an autoimmune disease or a circulatory disease.

Effect of the Invention

Using the methylated DNA-binding peptide of the present invention makes it possible to make an analysis while keeping the methylated DNA to be detected in the double-stranded structure as it is, with no special pretreatment required for the test sample. Also, actual reaction time is less than 30 minutes, and no special equipment is needed in the analytical step, nor is the test sample decomposed, so that the sample can be examined as it is. Therefore, the methylated DNA-binding molecule of the present invention makes it possible to detect and quantify methylated DNA in a short time, with saved labor, and without being limited by the nucleotide sequence of the methylated DNA to be detected.

Because the methylated DNA-binding peptide of the present invention is a small molecule such that the molecular weight thereof does not exceed 10000, it is unlikely to undergo steric hindrance in binding to the double-stranded DNA to be detected, and is highly versatile in the detection of methylated DNA, irrespective of whether it is used in a liquid phase system or a solid phase system. Also, the same is stabler in long-time storage than methylated DNA-binding protein (MBP) or an anti-methylated cytosine antibody, which has a high molecular weight; when used as a reagent, this can be supplied stably, and can be handled conveniently.

For the methylated DNA-binding peptide of the present invention, a chemical label may be added. This makes it possible to facilitate the detection of the peptide, and also to improve the quantitative analyzability. Depending on the type of label, it is possible to detect and quantify methylated DNA at high sensitivity; in addition to the detection and quantitation, it is also possible to confer new functions, such as the capability of inducing chemical reactions in the methylated region by binding to the DNA methylation region, to the methylated region.

DESCRIPTION OF EMBODIMENTS

Figure 1:
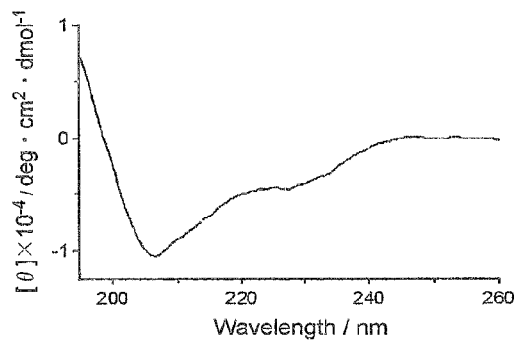
FIG. 1 shows the results of a CD spectrometry of 4 kinds of peptides. (A) shows the result for peptide Y (Example 1), (B) for peptide Y(PO3) (Example 2), (C) for peptide F (Comparative Example 1), and (D) for peptide Y(SO3) (Comparative Example 2); in each graph, the horizontal axis indicates wavelength (nm), and the vertical axis indicates mean residue ellipticity (deg cm² dmol⁻¹).
Figure 1:
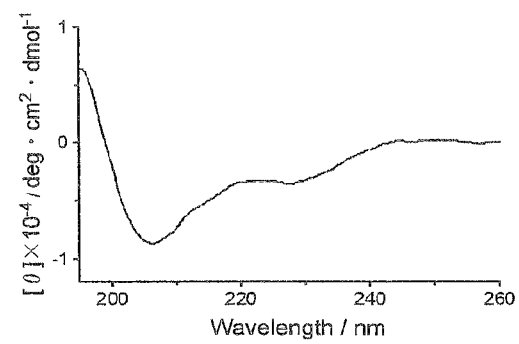
Figure 1:
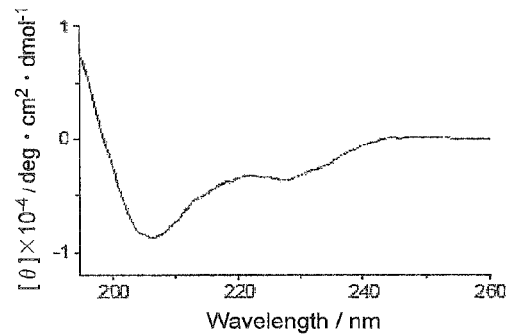
Figure 1:
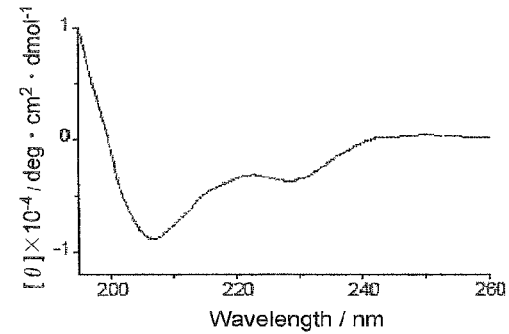

The present invention provides a peptide comprising a metal finger motif and a tyrosine derivative in a helix forming part of the motif, which recognizes and binds to a methylated region of a double stranded DNA.

In the present invention, the methylation of DNA refers to the phenomenon in which one or two or more DNA-constituting nucleotides are modified by a methyl group. The present invention is directed to 5-methylcytosine, resulting from the binding of a methyl group to the 5-position carbon of the cytosine residue, in particular. In the present invention, a metal finger motif refers to a particular amino acid sequence designed to bind to DNA by coordinately binding to a metal ion. The particular amino acid sequence may comprise an amino acid derivative in a portion thereof.

The structure of the metal finger motif is characterized in that the steric structure thereof changes upon coordination of a specified metal ion, resulting in a structure with a finger-like long loop protruding from the coordination moiety as the root. This structural change allows the metal finger motif to bind to double-stranded DNA, particularly to the major groove of double-stranded DNA. The total number of amino acid residues constituting the metal finger motif is not particularly limited, and can be, for example, 10 to 50 amino acid residues long, preferably 15 to 40 amino acid residues long, more preferably 20 to 35 amino acid residues long.

While a metal used for the metal finger is not particularly limited as long as it becomes a metal ion that can be coordinated with the motif, a metal that becomes a divalent cation is preferable. Examples thereof include zinc, cobalt, iron, cadmium, magnesium, manganese, calcium, strontium, barium, nickel, copper, mercury, tin, lead and the like. From the aspect of structural stability of the metal finger motif, the metal is preferably zinc, cobalt, iron, cadmium, magnesium, manganese or calcium, more preferably zinc, cobalt, iron or cadmium, particularly preferably zinc.

When using zinc as the metal, the metal finger may also be referred to as a zinc finger. Naturally occurring zinc fingers form a major superfamily of protein domains, each consisting of two antiparallel β sheets and one α helix, and possessing the property of binding to DNA by itself. Additionally, the molecular weight is small, and the zinc ion ($Zn^{2+}$) binds coordinately to the domain, whereby the structural stabilization of the zinc finger is maintained. Naturally occurring zinc fingers include those belonging to the $C_2H_2$ class, which contain two cysteines and two histidines, those belonging to the $C_4$ or $C_6$ class, which contain four cysteines or six cysteines, and the like; the metal finger motif of the present invention can also be categorized under such a class.

As stated above, a metal finger motif generally has a structure capable of binding to DNA; however, to confer thereto the property of selectively binding to a methylated region of DNA, it is necessary to design the same so that a tyrosine derivative is contained in the motif. Tyrosine is a kind of aromatic amino acid, having a phenol moiety in a side chain thereof. A tyrosine derivative is a compound modified to the extent that does not significantly change the structure or property of the main chain, such as introduction of a functional group into the tyrosine side chain, oxidation in the tyrosine side chain, reduction in the tyrosine side chain, or atom replacement in the tyrosine side chain. Upon introduction of a tyrosine derivative into the metal finger motif, the π electron derived from the aromatic ring on the side chain and the hydrogen atom derived from methylcytosine interact with each other (CH-π interaction), stabilizing the distance between the aromatic ring and the hydrogen atom and forming a kind of hydrogen bond to allow the metal finger motif to bind selectively to the DNA methylation region. This makes it possible to bind even to a double-stranded DNA methylation region, which is not achievable by prior art techniques.

From the viewpoint of bindability to double-stranded DNA, the tyrosine derivative is required to be arranged in a helix-forming portion of the metal finger motif in the present invention. The metal finger motif in the present invention is characterized by the formation of a helix (spiral); a helix-forming portion refers to a position of an amino acid residue that can correspond to the helix portion formed by the motif. Helices in the present invention include, for example, α helix, $3_{10}$ helix, π helix and the like, with preference given to α helix. The helix-forming portion in the present invention is a region unambiguously determined by the structure of the metal finger. In this region, the position of the tyrosine derivative is represented by, for example, $Xaa^2$ in the general formula (I) below; however, as far as it is within the helix-forming portion, the tyrosine derivative may be arranged in a position where it is on the same side in the helix as $Xaa^2$. The same side in the helix as $Xaa^2$ specifically refers to a position apart from the amino acid position of $Xaa^2$ by 3 to 5 amino acids or a number of amino acid residues that is a multiple thereof. Such a helical structure can be identified by X-ray diffraction, nuclear magnetic resonance (NMR), circular dichromatic (CD) spectrometry and the like. In CD spectrometry, in particular, a negative peak is detected in the vicinities of 208 nm and 222 nm, and a positive peak in the vicinity of 190 nm.

The metal finger motif in the present invention preferably contains a structure represented by the following formula (I):

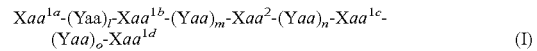

(I)

wherein $Xaa^{1a}$, $Xaa^{1b}$, $Xaa^{1c}$ and $Xaa^{1d}$ are the same or different and each is cysteine or histidine, $Xaa^2$ is tyrosine or a derivative thereof, Yaa is any amino acid, l is an integer of 2 or 4, m is an integer of 6-10, n is an integer of 2-4, and o is an integer of 3-5.

The structure of the above-mentioned formula (I) is constituted by the binding of various amino acids and tyrosine or a derivative thereof, where various binding modes are possibly taken, such as hydrogen bond, covalent bond, van der Waals bond, electrostatic interaction and the like. While the binding mode is not particularly limited in the present invention, the structure is preferably constituted by a covalent bond, particularly an amide bond, and further particularly preferably a peptide bond. While the amino acid encompasses an L form, a D form and a DL form, an L form is generally used, and the asymmetric center of the amino acid may be any of R-configuration, S-configuration and RS configuration.

The amino acid residues ($Xaa^{1a}$ and $Xaa^{1d}$) on the both ends constituting the structure represented by the above-mentioned formula (I) are each independently cysteine or histidine. In the metal finger motif in the present invention, the both ends may have any one or more amino acid residues or other molecules by additive binding. The structural stability and the like of a metal finger motif can be further improved by adding appropriate, given amino acid residues or other molecules to both ends by additive binding according to a method known per se.

$Xaa^{1a}$, $Xaa^{1b}$, $Xaa^{1c}$ and $Xaa^{1d}$ in the above-mentioned formula (I) are each independently cysteine (Cys) or histidine (His), and they may all be Cys, or conversely His. Since these Cys and His are amino acid residues directly involved in the coordinate binding of a metal ion, the positions thereof in the motif are particularly important for the metal finger motif in the present invention. In the present invention, Cys and His can be combined with $Xaa^{1a}$, $Xaa^{1b}$, $Xaa^{1c}$ and $Xaa^{1d}$ freely in the number and order, and the combination is not particularly limited. For example, two each of Cys and His are preferably used, and the order thereof is particularly preferably Cys, Cys, His, His in the order of $Xaa^{1a}$, $Xaa^{1b}$, $Xaa^{1c}$, $Xaa^{1d}$. A metal ion to be coordinated in this case is as described above, and zinc ion is most preferable.

$Xaa^2$ in the above-mentioned formula (I) is tyrosine or a derivative thereof. While the use of a tyrosine derivative in the metal finger motif in the present invention is explained above, when $Xaa^2$ is positioned as shown in the above-mentioned formula (I) constituted by plural amino acids, not only a tyrosine derivative but also tyrosine itself can provide the effect of the present invention. When a tyrosine residue is placed at this position, CH-π interaction is developed between π electron derived from an aromatic ring of the tyrosine residue side chain and methylated cytosine in the same manner as explained above, and a metal finger motif containing the structure of the above-mentioned formula (I) can selectively bind to the methylated region of a DNA. In the present invention, any residue can be used but a tyrosine derivative is preferable in view of the size of the CH-π interaction.

In the present invention, moreover, the structure of $(Yaa)_m$ in the aforementioned formula (I) can be shown by the following formula (II).

$$(Yaa)_{m1}\text{-}Xaa^{3a}\text{-}(Yaa)_{m2} \quad \text{(II)}$$

wherein $Xaa^{3a}$ is phenylalanine, tyrosine or leucine, Yaa is any amino acid, m1 is an integer of 2-4, and m2 is an integer of 3-5.

In the present invention, moreover, the structure of $(Yaa)_n$ in the aforementioned formula (I) can be shown by the following formula (III).

$$Xaa^{3b}\text{-}(Yaa)_{n1} \quad \text{(III)}$$

wherein $Xaa^{3b}$ is phenylalanine, tyrosine or leucine, Yaa is any amino acid, and n1 is an integer of 1-3.

The above-mentioned formulas (II) and (III) are both characteristically constituted by an amino acid selected from phenylalanine, tyrosine and leucine, and one or more optional amino acids, where various binding modes are possibly taken, as in the above-mentioned formula (I). Of such binding modes, amide bond is preferable and peptide bond is particularly preferable, as in the above-mentioned formula (I). While the amino acid encompasses an L form, a D form and a DL form, an L form is generally used, and the asymmetric center of the amino acid may be any of R-configuration, S-configuration and RS configuration.

In the present invention, an amino acid selected from phenylalanine, tyrosine and leucine is characteristically placed at the positions of $Xaa^{3a}$ and $Xaa^{3b}$ in the above-mentioned formula (I), as shown in the above-mentioned formulas (II) and (III). These amino acid residues form a hydrophobic core, and also form a hydrophobic interaction. Therefore, the structure of the metal finger motif in the present invention can be further stabilized by placing phenylalanine, tyrosine or leucine as mentioned above. The structure wherein the above-mentioned formulas (II) and (III) are incorporated in the above-mentioned formula (I) can be shown by the following formula (VIII).

$$Xaa^{1a}\text{-}(Yaa)_l\text{-}Xaa^{1b}\text{-}(Yaa)_{m1}\text{-}Xaa\text{-}(Yaa)_{m2}\text{-}Xaa^2\text{-}\\Xaa^{3b}\text{-}(Yaa)_{n1}\text{-}Xaa^{1c}\text{-}(Yaa)_o\text{-}Xaa^{1d} \quad \text{(VIII)}$$

wherein $Xaa^{1a}$, $Xaa^{1b}$, $Xaa^{1c}$ and $Xaa^{1d}$ are the same or different and each is cysteine or histidine, $Xaa^2$ is tyrosine or a derivative thereof, $Xaa^{3a}$ and $Xaa^{3b}$ are each independently phenylalanine, tyrosine or leucine, Yaa is any amino acid, l is an integer of 2 or 4, m1 is an integer of 2-4, m2 is an integer of 3-5, n1 is an integer of 1-3, and o is an integer of 3-5.

In the present invention, moreover, the structure of $(Yaa)_{m1}$ in the aforementioned formula (II) or (VIII) can be shown by the following formula (IV).

$$(Yaa)_{m3}\text{-}Xaa^{4a}\text{-}(Yaa)_{m4} \quad \text{(IV)}$$

wherein $Xaa^{4a}$ is lysine, arginine or histidine, Yaa is any amino acid, and m3 and m4 are each an integer of 0-2.

In the present invention, moreover, the structure of $(Yaa)_{n1}$ in the aforementioned formula (III) or (VIII) can be shown by the following formula (V).

$$(Yaa)_{n2}\text{-}Xaa^{4b} \quad \text{(V)}$$

wherein $Xaa^{4b}$ is lysine, arginine or histidine, Yaa is any amino acid, and n2 is an integer of 0-2.

The above-mentioned formulas (IV) and (V) are both characteristically constituted only by an amino acid selected from lysine, arginine and histidine, or such amino acid added with one or more optional amino acids. When constituted by plural amino acids, various binding modes of amino acids are possibly taken, as in the above-mentioned formula (I). Of such binding modes, amide bond is preferable and peptide bond is particularly preferable, as in the above-mentioned formula (I). While the amino acid encompasses an L form, a D form and a DL form, an L form is generally used, and the asymmetric center of the amino acid may be any of R-configuration, S-configuration and RS configuration.

Lysine, arginine and histidine are positively-charged or hydrogen-donating amino acids and, in the present invention, these amino acids are characteristically placed at the positions of $Xaa^{4a}$ and $Xaa^{4b}$ in the above-mentioned formula (VIII), as shown in the above-mentioned formulas (IV) and (V). These residues interact with a tyrosine derivative to impart a fixed structure suitable for CH-π interaction to the tyrosine derivative, as well as interact with the tyrosine derivative and a double stranded DNA to stabilize a complex of a metal finger motif in the present invention and the double stranded DNA. Therefore, the conformation of tyrosine or a derivative thereof contained in the metal finger motif in the present invention can be further fixed by placing lysine, arginine or histidine as mentioned above, and the effect of binding to a methylated DNA can be further enhanced. The structure wherein the above-mentioned formulas (IV) and (V) are incorporated in the above-mentioned formula (VIII) can be shown by the following formula (IX).

$$Xaa^{1a}\text{-}(Yaa)_l\text{-}Xaa^{1b}\text{-}(Yaa)_{m3}\text{-}Xaa^{4a}\text{-}(Yaa)_{m4}\text{-}Xaa^{3a}\text{-}\\(Yaa)_{m2}\text{-}Xaa^2\text{-}Xaa^{3b}\text{-}(Yaa)_{n2}\text{-}Xaa^{4b}\text{-}Xaa^{1c}\text{-}\\(Yaa)_o\text{-}Xaa^{1d} \quad \text{(IX)}$$

wherein $Xaa^{1a}$, $Xaa^{1b}$, $Xaa^{1c}$ and $Xaa^{1d}$ are the same or different and each is cysteine or histidine, $Xaa^2$ is tyrosine or a derivative thereof, $Xaa^{3a}$ and $Xaa^{3b}$ are each independently phenylalanine, tyrosine or leucine, $Xaa^{4a}$ and $Xaa^{4b}$ are each independently lysine, arginine or histidine, Yaa is any amino acid, l is an integer of 2 or 4, m3 and m4 are each an integer of 0-2, m2 is an integer of 3-5, n2 is an integer of 0-2, and o is an integer of 3-5.

In the present invention, moreover, the structure of (Yaa) in the aforementioned formula (II), (VIII) or (IX) can be shown by the following formula (VI).

$$(Yaa)_{m5}\text{-}Xaa^{4c}\text{-}(Yaa)_{m6} \quad (VI)$$

wherein $Xaa^{4c}$ is arginine, Yaa is any amino acid, m5 is an integer of 0-2, and m6 is an integer of 1-3.

The above-mentioned formula (VI) is characteristically constituted by arginine and one or more optional amino acids. Various binding modes of amino acids are possibly taken, as in the above-mentioned formula (I). Of such binding modes, amide bond is preferable and peptide bond is particularly preferable, as in the above-mentioned formula (I). While the amino acid encompasses an L form, a D form and a DL form, an L form is generally used, and the asymmetric center of the amino acid may be any of R-configuration, S-configuration and RS configuration.

In the present invention, arginine is characteristically placed at the position of $Xaa^{4c}$ in the above-mentioned formula (II), (VIII) or (IX), as shown in the above-mentioned formula (VI). Since arginine is an amino acid showing high affinity for guanine (G) in CpG island, the affinity for a double stranded DNA to be detected can be improved by placing arginine as mentioned above, and the binding force of the metal finger motif in the present invention to a double stranded DNA can be further enhanced. The structure wherein the above-mentioned formula (VI) is incorporated in the above-mentioned formula (IX) can be shown by the following formula (X).

$$Xaa^{1a}\text{-}(Yaa)_l\text{-}Xaa^{1b}\text{-}(Yaa)_{m3}\text{-}Xaa^{4a}\text{-}(Yaa)_{m4}\text{-}Xaa^{3a}\text{-}(Yaa)_{m5}\text{-}Xaa^{4c}\text{-}(Yaa)_{m6}\text{-}Xaa^{2}\text{-}Xaa^{3b}\text{-}(Yaa)_{n2}\text{-}Xaa^{4b}\text{-}Xaa^{1c}\text{-}(Yaa)_{o}\text{-}Xaa^{1d} \quad (X)$$

wherein $Xaa^{1a}$, $Xaa^{1b}$, $Xaa^{1c}$ and $Xaa^{1d}$ are the same or different and each is cysteine or histidine, $Xaa^2$ is tyrosine or a derivative thereof, $Xaa^{3a}$ and $Xaa^{3b}$ are each independently phenylalanine, tyrosine or leucine, $Xaa^{4a}$ and $Xaa^{4b}$ are each independently lysine, arginine or histidine, $Xaa^{4b}$ is arginine, Yaa is any amino acid, l is an integer of 2 or 4, m3 and m4 are each an integer of 0-2, m5 is an integer of 0-2, m6 is an integer of 1-3, n2 is an integer of 0-2, and o is an integer of 3-5.

The tyrosine derivative contained in the metal finger motif in the present invention is not particularly limited as long as it is a compound obtained by alteration of tyrosine as a matrix to the extent that does not drastically change the structure and properties of the matrix, such as introduction of functional group, oxidation, reduction, substitution of atom and the like. It is preferably a compound represented by the following formula (VII).

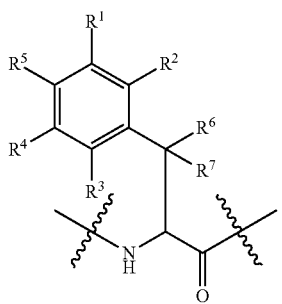

(VII)

wherein
$R^1$, $R^2$, $R^3$, $R^4$ and $R^5$ are each independently a hydrogen atom, a halogen atom, an alkyl group, an alkoxy group, a nitro group, an amino group or a phosphorus-containing group,
when $R^1$ and $R^2$, as well as $R^3$ and $R^4$, are not phosphorus-containing groups, they may be respectively joined to form an aromatic ring or aromatic heterocycle, and
at least one of $R^1$, $R^2$, $R^3$, $R^4$ and $R^5$ is a phosphorus-containing group, and
$R^6$ and $R^7$ are each independently a hydrogen atom, a halogen atom, an alkyl group, an alkoxy group, a nitro group, an amino group or a phosphorus-containing group.

The halogen atom for $R^1$, $R^2$, $R^3$, $R^4$, $R^5$, $R^6$ or $R^7$ is not particularly limited and, for example, fluorine atom, chlorine atom, bromine atom, iodine atom and the like can be mentioned. The alkyl group may be linear or branched chain and, for example, a lower alkyl group having a carbon number of 1-6 can be mentioned. Examples thereof include, but are not particularly limited to, methyl group, ethyl group, n-propyl group, isopropyl group, n-butyl group, isobutyl group, sec-butyl group, tert-butyl group, pentyl group, hexyl group and the like. Examples of the alkoxy group include a lower alkoxy group having a carbon number of 1-6, and examples thereof include, but are not particularly limited to, methoxy group, ethoxy group, propoxy group, isopropoxy group, butoxy group, isobutoxy group, sec-butoxy group, tert-butoxy group, pentoxy group, hexyloxy group and the like can be mentioned.

The phosphorus-containing group for $R^1$, $R^2$, $R^3$, $R^4$, $R^5$, $R^6$ or $R^7$ refers to a chemical group comprising a phosphorus atom (P), and the phosphorus atom may be trivalent or pentavalent. The phosphorus-containing group in the present invention is not particularly limited as long as it includes a phosphorus atom bonded to an oxygen atom, a hydrogen atom, a nitrogen atom, a sulfur atom, a carbon atom, a halogen atom and the like. Examples thereof include phosphate group, diphosphate group, triphosphate group, pyrophosphate group, alkylphosphate group, phosphorothioate group, phosphorodithioate group, phosphoroamidate group and the like. For example, when a degrading enzyme such as phosphatase and the like is present in a sample containing methylated DNA to be detected, a phosphorothioate group and the like, which are resistant to the decomposition, is preferably used. In the present invention, at least one of the substituents for $R^1$-$R^5$ is a phosphorus-containing group, preferably, a phosphorus-containing group is only one and the rest is not a phosphorus-containing group. More preferably, only the substituent for $R^5$ is a phosphorus-containing group, and the rest of the substituent is a chemical group other than the phosphorus-containing group, or form an aromatic ring or aromatic heterocycle. Of these, a phosphate group is particularly preferable from among the phosphorus-containing groups.

When each of $R^1$, $R^2$, $R^3$ and $R^4$ is not a phosphorus-containing group, $R^1$ and $R^2$, as well as $R^3$ and $R^4$, can be joined to form an aromatic ring or aromatic heterocycle. Here, the aromatic ring refers to a ring having an unsaturated cyclic structure wherein atoms having π electron are arranged in a cycle, and the number of electrons contained in the π electron system on the ring is 4n+2 (n is an integer of not less than 0). An aromatic heterocycle refers to, of the aforementioned aromatic rings, an aromatic ring containing an atom other than carbon atom, which is also referred to as hetero atom, as a constituent element. In the present invention, these aromatic rings and aromatic heterocycles include not only monocyclic ones but also polycyclic structures such as bicyclic one and one with higher polycyclicity. The aromatic ring and aromatic heterocycle are not particularly limited, and examples thereof include rings formed by benzene, furan, naphthalene, anthracene, phenanthrene, tetracene, chrysene, triphenylene, tetraphene, pyrene, pentacene, picene, perylene, pyridine, quinoline, isoquinoline, pyrazine, quinoxaline, acridine, pyrimidine, quinazoline, pyridazine, cinnoline, triazine, benzofuran, isobenzofuran, pyrrole, indole, isoindole, thiophene, benzothiophene, imidazole, benzoimidazole, purine, pyrazole, indazole, oxazole, benzooxazole, isoxazole, benzoisoxazole, thiazole, benzothiazole and the like.

The peptide of the present invention characteristically contains a particular metal finger motif as the above. The peptide of the present invention can be exchangeably expressed by the terms "peptide", "polypeptide" and "protein", and is constituted by two or more amino acids linked by an amide bond (peptide bond) and the like. While the amino acid encompasses an L form, a D form and a DL form, an L form is generally used, and the asymmetric center of the amino acid may be any of R-configuration, S-configuration and RS configuration.

The peptide of the present invention can have any length of amino acid residues. For example, it can have 5-100, preferably 15-80, more preferably 20-70, amino acid residue length. The molecular weight of the peptide can be determined according to the length of the amino acid residues, and is not particularly limited. For example, it may be less than 10000, preferably less than 8000, more preferably less than 6000, particularly preferably less than 4000.

The peptide of the present invention can contain, in addition to the above-mentioned one kind of metal finger motif, one or more of a metal finger motif having an amino acid sequence the same as or different from that of the metal finger motif, or a metal finger motif that does not recognize methylated DNA but binds to unmethylated DNA. In addition, it is possible to contain not only a metal finger motif but also, for example, a DNA-binding motif such as leucine zipper, helix-turn-helix (HTH) and the like. These DNA-binding motifs can be used alone or in a combination of two or more kinds thereof. The above-mentioned metal finger motifs can be directly linked to such DNA-binding motifs, or via one or more amino acid residues or other molecules and the like. The presence of such DNA-binding motif affords high DNA affinity as well as confers a function to recognize a particular base sequence including methylcytosine.

When the peptide of the present invention contains plural metal finger motifs and/or other DNA-binding motif, the order of such motifs from the N-terminal is not particularly limited.

The N-terminal and C-terminal of the peptide of the present invention may be modified. As the modification, modifications generally employed for stabilizing peptide, functional regulation, induction of chemical reaction and the like can, be used without limitation. Examples of the modification of N-terminal include acylation such as acetylation, benzoylation and the like, formylation, myristoylation, methylation, pyroglutamate modification, glycation, biotinylation, dye modification such as fluorescence labeling and the like, and the like, and examples of the modification of C-terminal include amidation, SUMOylation, GPI anchoring, biotinylation, dye modification such as fluorescence labeling and the like, and the like.

The peptide of the present invention may include a salt thereof. Examples of the salt of peptide include salts with inorganic acids (e.g., hydrochloric acid, phosphoric acid, hydrobromic acid, sulfuric acid etc.), salts with organic acids (e.g., acetic acid, formic acid, propionic acid, fumaric acid, maleic acid, succinic acid, tartaric acid, citric acid, malic acid, oxalic acid, benzoic acid, methanesulfonic acid, benzenesulfonic acid etc.), salts with bases (e.g., alkali metals (e.g., sodium, potassium etc.), alkaline earth metals (e.g., calcium, magnesium etc.), ammonium and substituted ammonium (e.g., dimethylammonium triethylammonium etc.) and the like.

The peptide of the present invention is not limited to those constituted by amino acid alone, and includes one containing the above-mentioned metal finger motif to which a molecule other than amino acid is directly bound or bound via one or more amino acid residues. Examples of such other molecule include photoreactive molecules having an orthonitrobenzyl group, a diazo group, an azo compound and the like, intercalators (e.g., anthracene, ethidium etc.), signal molecules (e.g., quantum dot, fluoride, gadolinium ion and chelator thereof etc.), solid phase carriers (e.g., magnetic particles, plastic, gel etc.) and the like. It may also be other peptide (protein), such as antibody, carrier protein and the like. Using, as such other molecule, a natural compound, a chemically synthesized compound and the like that characteristically bind to DNA, the DNA binding affinity of the peptide of the present invention can be further enhanced.

The peptide of the present invention can be further labeled with a labeling agent. Examples of the label to be used in the present invention include radioisotope, enzyme, fluorescent substance, luminescence substance, hapten and the like. Examples of the radioisotope include $^{32}P$, $^{33}P$, $^{35}S$, $^{3}H$, $^{14}C$, $^{65}Zn$, $^{57}Co$, $^{59}Fe$, $^{109}Cd$, $^{28}Mg$, $^{54}Mn$, $^{45}Ca$, $^{90}Sr$, $^{133}Ba$, $^{63}Ni$, $^{64}Cu$, $^{203}Hg$, $^{113}Sn$, $^{202}Pb$ and the like, which can be purchased from Japan Radioisotope Association etc. as appropriate. Metal radioisotopes such as $^{65}Zn$, $^{57}Co$, $^{59}Fe$, $^{109}Cd$, $^{28}Mg$, $^{54}Mn$, $^{45}Ca$, $^{90}Sr$, $^{133}Ba$, $^{63}Ni$, $^{64}Cu$, $^{203}Hg$, $^{113}Sn$, $^{202}Pb$ and the like may be used to label a metal finger motif in the present invention by coordination in the form of a metal ion. As the enzyme, a stable enzyme having high specific activity is preferable and, for example, β-galactosidase, β-glucosidase, alkaliphosphatase, peroxidase, malic acid dehydrogenase and the like are used. Examples of the fluorescent substance include fluorescein, fluorescamine, fluorescein isothiocyanate and the like. Examples of the luminescence substance include luminol, luminol derivative, luciferin, lucigenin and the like. As the hapten, biotin, digoxygenin, dinitrophenol (DNP), thymine dimer and the like are used. Using them, a methylated region of a DNA can be detected or quantified via the peptide of the present invention, and the detection sensitivity thereof can also be improved.

The method of producing a peptide of the present invention is not particularly limited; the peptide can be chemically or biologically produced by a publicly known method of peptide synthesis (peptide chain synthesis). As a method of peptide synthesis, for example, a method is used wherein an amino acid having the carboxyl group protected (amino component) is reacted with an amino acid having the amino group protected (acid component), and the free amino group and carboxyl group are dehydration-condensed using dicyclohexylcarbodiimide and the like to synthesize a peptide linkage, and, after the reaction, the protecting group is removed. In this operation, by removing the protecting group for the amino group only, adding a new acid component, carrying out the reaction, and repeating this cycle, it is possible to elongate amino acids one by one from the C-terminal side to the N-terminal side. Not only adding amino acids one by one, but also a method can also be used wherein peptides with a certain length (oligopeptides) are bound together. This method of peptide synthesis may be performed by either solid phase synthesis performed on an insoluble polymer carrier, or liquid phase synthesis performed in solution. Protecting groups for the N-amino group that can be used include the t-butoxycarbonyl (Boc) group, the 9-fluorenylmethoxycarbonyl (Fmoc)

group and the like. These methods of peptide synthesis can be performed using a commercially available automated peptide synthesizer.

Other methods include production of a peptide of the present invention using a publicly known gene recombination technique. In this case, by, for example, first acquiring a polynucleotide that encodes a peptide of the present invention, transforming the host with an expression vector containing the polynucleotide, and culturing the transformant obtained, the peptide can be produced.

The polynucleotide may be DNA or RNA, or a DNA/RNA chimera, and is preferably DNA. Also, the polynucleotide may be double-stranded or single-stranded. If double-stranded, the polynucleotide may be double-stranded DNA, double-stranded RNA, or a DNA:RNA hybrid. The polynucleotide can be directly amplified by PCR using an appropriate primer designed by means of publicly known sequence information and the like, with a DNA clone or the like as the template. For example, when the metal finger of the present invention is a zinc finger, a base sequence contained in a transcription regulatory factor (for example, Sp1 and the like) in many biological species, including humans, can be utilized as the sequence information; furthermore, by utilizing site-directed mutagenesis and the like, tyrosine can be introduced into a specified position. Besides, on the basis of the sequence information, the polynucleotide may be synthesized using a commercially available polynucleotide synthesizer.

Vectors include expression vectors, cloning vectors and the like, and can be chosen according to the purpose. The expression vector can be produced by functionally joining the polynucleotide downstream of a promoter in an appropriate expression vector. Useful kinds of vectors include plasmid vectors, viral vectors and the like, and can be chosen as appropriate according to the host used.

By introducing the vector into a host according to a method of gene transfection known per se (for example, lipofection, calcium phosphate method, microinjection, protoplast fusion, electroporation, DEAF dextran method, gene transfection using a gene gun, and the like), a transformant incorporating the vector can be produced. By using an expression vector as the vector to be introduced, the transformant is allowed to express a peptide of the present invention. By culturing the transformant using a method known per se according to the type of the host, and isolating a peptide of the present invention from the culture, the peptide of the present invention can be produced.

The peptide obtained as mentioned above can be isolated and purified by a combination of conventional purification methods, for example, solvent extraction; distillation; plural chromatographys such as reversed-phase chromatography, ion exchange chromatography, gel filtration chromatography, affinity chromatography, high performance liquid chromatography (HPLC) and the like; recrystallization and the like. When the peptide obtained by the above-mentioned method is a free form, it can be converted to a suitable salt by a known method. When it is conversely obtained as a salt, it can also be converted to a free form by a known method.

In the tyrosine derivative represented by the above-mentioned formula (VII), a phosphorus-containing group can be introduced into the position of $R^5$ in the above-mentioned formula (VII) by modifying a peptide synthesized as mentioned above with a phosphorylation enzyme (also referred to as kinase, phosphokinase, protein kinase) or an amidite reagent. When a phosphorylation enzyme is used, for example, a phosphorus-containing group can be introduced into a tyrosine residue of the peptide by a method known per se and concurrently using a donor of a phosphorus-containing group such as ATP and the like, and a metal ion such as magnesium ion, manganese ion and the like.

When a tyrosine derivative or a non-natural amino acid having a fluorescent group or biotin and the like in a side chain thereof is introduced into a peptide of the present invention, a method of protein synthesis involving introduction of a non-natural amino acid (CloverDirect™, ProteinExpress) can be used. The method of synthesis can be performed by utilizing the UAG codon (amber codon) or the CGGG codon (4-base codon), which are stop codons.

Specifically explaining a case wherein an amber codon is used, the UAG codon is inserted into, or substituted for, the site to introduce a non-natural amino acid thereinto in the gene that encodes a peptide of the present invention to construct an mRNA, and the mRNA, along with an amber suppressor tRNA having the non-natural amino acid bound thereto, is added to a cell-free translation system, whereby the tRNA will read the UAG codon, resulting in the introduction of the non-natural amino acid into the specified position. Here, an amber suppressor tRNA refers to a factor that reads the amber codon (UAG) resulting from a mutation or the like as a codon (sense codon) corresponding to an amino acid, and restores and continues the protein synthesis that will otherwise be interrupted or completed. If this UAG codon is read by a termination factor, the peptide synthesis will stop at that time; therefore, provided that the full-length peptide alone is isolated after the reaction completes itself, a desired peptide incorporating a non-natural amino acid at high efficiency can be obtained.

When using the CGGG codon, the CGGG codon is inserted into, or substituted for, the site to introduce a non-natural amino acid thereinto in the gene that encodes a peptide of the present invention to construct an mRNA, and the mRNA, along with a tRNA containing the 4-base anticodon CCCG, and having the non-natural amino acid bound thereto, is added to a cell-free translation system, whereby the tRNA will read the CGGG codon, resulting in the introduction of the non-natural amino acid into the specified position. In this case, if the codon is read by Arg-tRNA, which recognizes the CGG codon, the reading frame for the codon is shifted, and peptide synthesis is terminated by a downstream stop codon; however, because the CGG codon is a codon of generally low frequency of use (minor codon), the reading is unlikely to occur. Thereby, it is possible to obtain a desired peptide incorporating the non-natural amino acid introduced into the specified position.

The present invention also provides the above-described peptide that contains a metal ion in a coordinately linked state. The metal finger motif contained in the peptide of the present invention is characterized in that the steric structure changes as the metal ion is coordinated to the motif. The post-change steric structure can be identified by the obtainment of a negative signal in the vicinities of 222 nm and 208 nm and a positive signal in the vicinity of 190 nm using a measuring method utilizing circular polarization dichroism (also called circular dichroism (CD)). This steric structural change further increases the bindability to DNA methylation regions (methylcytosine). Also, the peptide of the present invention, along with a metal ion, is supplied to detect methylated DNA, and, while with the metal ion coordinated, does not require the metal ion to be supplied separately, and allows the detecting operation by a single treatment.

While the metal ion is not particularly limited as long as it can coordinately binds to a metal finger motif, a metal ion that becomes a divalent cation is preferable and, for example, zinc ion, cobalt(II) ion, ferrous ion, cadmium ion, magnesium ion, manganese ion, calcium ion, strontium ion, barium ion, nickel ion, copper ion, mercury ion, tin ion, lead ion and the like can be mentioned. Of these, zinc ion, cobalt(II) ion, ferrous ion, cadmium ion, magnesium ion, manganese ion and calcium ion are preferable, zinc ion, cobalt(II) ion, ferrous ion and cadmium ion are more preferable, and zinc ion is particularly preferable as the metal ion, from the aspect of structural stability of the metal finger motif. When the metal ion is a cobalt(II) ion, the binding and structure of the peptide of the present invention and cobalt(II) ion can be confirmed by the measurement of ultraviolet visible absorption spectrum which shows an absorption band at 320 nm, which corresponds to a charge transfer absorption band (Ligand to Metal Charge Transfer (LMCT) band) of ligand to the central metal, and absorption bands centering around 582 nm and 640 nm, which correspond to d-d transition.

The present invention also provides a kit for detecting a methylated region of a double stranded DNA, comprising the above-mentioned peptide and a metal ion supply compound. To bind to a methylated region of a DNA, the metal finger motif in the present invention is required to change its structure by coordination of a metal ion. Therefore, it is preferable to simultaneously use a compound capable of supplying a metal ion and the peptide of the present invention. Thus, using the kit of the present invention, a methylated region of a DNA can be detected efficiently.

While the metal ion supply compound in the present invention is not particularly limited as long as it supplies a metal ion that coordinately binds to the above-mentioned metal finger motif, a compound that supplies a metal ion that becomes a divalent cation is preferable. Examples thereof include compounds containing a metal atom such as zinc, cobalt, iron, cadmium, magnesium, manganese, calcium, strontium, barium, nickel, copper, mercury, tin, lead and the like. Of these, zinc, cobalt, iron, cadmium, magnesium, manganese and calcium are preferable, zinc, cobalt, iron and cadmium are more preferable, and zinc is particularly preferable as the metal atom, from the aspect of structural stability of the metal finger motif. Examples of the metal ion supply compound include a salt containing the above-mentioned metal atom and the like, and examples of the salt include salts with inorganic acids (e.g., hydrochloric acid, phosphoric acid, hydrobromic acid, sulfuric acid etc.), salts with organic acids (e.g., acetic acid, formic acid, propionic acid, fumaric acid, maleic acid, succinic acid, tartaric acid, citric acid, malic acid, oxalic acid, benzoic acid, gluconic acid, methanesulfonic acid, benzenesulfonic acid etc.). When the metal atom is a zinc atom, examples of the metal ion supply compound include zinc chloride, zinc sulfate, zinc acetate, zinc citrate, zinc lactate, zinc gluconate and the like, of which zinc chloride, zinc sulfate, zinc acetate and zinc citrate are preferable, and zinc chloride is more preferable. In the present invention, such metal ion supply compound may be used alone or in a combination of two or more kinds thereof.

The present invention also provides a method of detecting a double-stranded DNA methylation region, comprising (a) a step of contacting the above-described peptide with no metal ion coordinated thereto, a metal ion supplying compound, and double-stranded DNA, and (c) a step of detecting the peptide bound to the double-stranded DNA methylation region. As stated above, for the peptide containing a metal finger motif in the present invention to bind to methylated DNA, the metal ion is required to be coordinated to the motif. For this reason, the method of the present invention for detection of methylated DNA is characterized in that a peptide with no metal ion coordinated thereto and a compound that supplies a metal ion that coordinately binds thereto are used in combination. The peptide and the metal ion supplying compound may be added simultaneously to the sample containing methylated DNA, or the peptide may be added in advance with the metal ion supplying compound added thereafter, or the order of addition may be the reverse.

The present invention also provides a method of detecting a double-stranded DNA methylation region, comprising (b) a step of contacting the above-described peptide with a metal ion already coordinated thereto and double-stranded DNA, and (c) a step of detecting the peptide bound to the double-stranded DNA methylation region. According to the present invention, because the metal ion is already coordinated to the peptide, and also because the peptide has already assumed a structural mode capable of binding to methylated DNA, it is possible to detect the double-stranded DNA methylation region without separately using a metal ion supplying compound.

In the present invention, the sample containing the double-stranded DNA to be detected is not subject to limitation as to the derivation thereof, and may be derived from any organism, preferably from a mammal (for example, humans, mice, rats, monkeys, dogs, bovines, horses, swine, sheep, goat, rabbits, hamsters and the like), more preferably humans, mice, rats, monkeys, dogs, particularly preferably humans.

Samples containing double-stranded DNA are exemplified by mammalian tissues (for example, brain or any portion of the brain (e.g., olfactory bulb, amygdaloid nucleus, basal ganglia, hippocampus, thalamus, hypothalamus, cerebral cortex, medulla oblongata, cerebellum), spinal cord, hypophysis, stomach, pancreas, kidney, liver, gonad, thyroid, gallbladder, bone marrow, adrenal gland, skin, lung, gastrointestinal tract (e.g., large intestine, small intestine), blood vessel, heart, thymus, spleen, submandibular gland, blood (e.g., peripheral blood, cord blood), prostate, testicle, ovary, placenta, uterus, bone, hair, joint, adipose tissue, skeletal muscle and the like), or cells isolated from the tissue (for example, hepatocyte, splenocyte, nerve cell, glial cell, pancreatic β cell, myelocyte, mesangial cell, Langerhans' cell, epidermal cell, epithelial cell, goblet cell, endothelial cell, smooth muscle cell, fibroblast, fibrocyte, myocyte, adipocyte, immune cells (e.g., macrophage, T cell, B cell, natural killer cell, mast cell, neutrophil, basophil, eosinophil, monocyte), megakaryocyte, synovial cell, chondrocyte, bone cell, osteoblast, osteoclast, mammary gland cell, hepatocyte or interstitial cell, or corresponding precursor cell, stem cell or cancer cell thereof, and the like), as well as urine, sputum, semen and the like.

The sample containing double-stranded DNA may be one of the above-described biological samples as it is, or may be DNA isolated from the biological sample. Examples of methods of DNA isolation (extraction) include a method wherein the cell protein is lysed using proteinase K and a lysis buffer (50 mM Tris-HCl (pH 7.5), 20 mM EDTA, 0.1 M NaCl, 1% SDS) and the like, and DNA is extracted using phenol/chloroform, a method wherein DNA is extracted using a commercially available DNA extraction reagent, a method of extraction using a column kit (GENERATION Capture Column Kit Gentra, Qiagen) and the like; and the isolation (extraction) can be achieved according to a method known per se.

The step for contacting the peptide and the like and double-stranded DNA in (a) or (b) above is not particularly limited as to the method of contact; the step may be in a mode wherein the required components are added to the liquid and allowed to react therein (liquid phase system), or may be in a mode wherein the required components have been immobilized on a solid phase, and another component is added to the immobilized components (solid phase system). In the step of detecting the peptide in (c) above, the method of detection thereof is not particularly limited, and any method can be utilized.

In a method of detection in a liquid phase system, first, for example, either the above-described peptide with no metal ion coordinated thereto and a metal ion supplying compound, or the above-described peptide with a metal ion already coordinated thereto, and a test sample, i.e., a sample containing double-stranded DNA, is added to a solution such as a buffer solution, whereby they can be contacted with each other. In this operation, the sample containing double-stranded DNA is not particularly limited, but it is preferable to use a DNA extract isolated from a tissue or cell. Examples of buffer solutions include phosphate buffer solutions, acetic acid buffer solutions, citrate buffer solutions, Tris-HCl buffer solutions, phosphate-buffered saline, Tris buffered physiological saline and the like. Here, it is preferable that a chelating agent such as EDTA be not added. This is because the metal ion used in the present invention is feared to fail to be coordinated to the peptide due to addition of the chelating agent. In these solutions, contact time is not particularly limited, as far as it allows the peptide and the double-stranded DNA methylation region to bind to each other, but it is preferable that the contact time be 1 to 30 minutes under 0 to 50° C. conditions. The order of adding the peptide and the like is not particularly limited, and they may be added simultaneously.

After contacting the peptide and the test sample, the peptide can be detected by utilizing, for example, fluorescence polarization, fluorescent correlation spectroscopy or isothermal titration calorimetry and the like.

Fluorescence polarization is the method wherein the state of a molecule is determined by utilizing the phenomenon where the polarity of the resulting fluorescence varies depending on the state of the molecule when applying polarized light as exciting light to a fluorophore, (fluorescence anisotropy). For this reason, the peptide need to be labeled with a fluorophore such as fluorescein, fluorescamine, or fluorescein isothiocyanate in advance before being contacted with the sample containing double-stranded DNA. The fluorophore label can be conferred by a method known per se; for example, when using a commercially available fluorophore, this labeling can be achieved according to the instruction manual protocol contained in the product. A measurement of fluorescence polarization can be achieved by exciting the fluorophore at a particular wavelength suitable therefor, and detecting the particular wavelength using a commercially available plate reader.

Fluorescent correlation spectroscopy is a method used to examine the molecular movements of fluorophores by measuring the fluctuation of fluorescence intensity with light of particular wavelength applied to a minute range of the sample by means of the autocorrelation of fluorescence. Therefore, it is necessary to fluorescently label the peptide in advance in the same manner as the above; after contacting with double-stranded DNA, using, for example, a light microscope, preferably a confocal microscope or a two-photon microscope and the like, and a commercially available apparatus for detection, the fluctuation of fluorescence intensity may be examined, and while obtaining time spectrum by inverse Fourier transformation of the intensity spectrum, the status of movement of the fluorophore and the number can be determined.

Isothermal titration calorimetry is to detect a calorific change with titration at a constant temperature; the small calorific change produced upon binding of the peptide and double-stranded DNA is measured, and the binding ratio, binding constant, and binding enthalpy change are determined from the titration curve obtained, whereby the binding state of the two molecules can be examined. Apparatuses for measuring the calorie generated with isothermal titration include commercially available isothermal titration calorimeters and the like, and are exemplified by apparatuses from MicroCal Company, TA INSTRUMENTS Company and the like.

In another mode of detection in a liquid phase system, gel shift assay can also be utilized.

When utilizing gel shift assay, the peptide of the present invention need to have been given a label before being contacted with double-stranded DNA. Here, the label is not particularly limited; radioisotopes such as $^{32}P$, fluorophores such as fluorescein, haptens such as digoxigenin and biotin, and the like can be used, and the label can be added by a method known per se. After contacting the peptide given the label and the double-stranded DNA, electrophoresis is performed on the basis of a conventional publicly known technique using, for example, polyacrylamide gel and the like. After performing the electrophoresis, the migrated substance is transferred from the gel used to a nylon membrane or the like, and the band obtained is examined. Regarding the method of the examination thereof, when using a radioisotope to label the peptide, for example, the band is detected using autoradiography and the like; when using a fluorophore, the detection can be achieved by applying light with a particular wavelength; when using a hapten, the detection can be achieved by detecting the fluorescence of an immune reaction using a substance that binds to the hapten (antibody, streptavidin and the like) and a fluorescently labeled antibody that recognizes the binding substance.

On the other hand, as a method of detection in a solid phase system, for example, in situ detection of methylated DNA and the like can be utilized. In this case, first, the tissue or cell to be the specimen is immobilized on a solid support while in a state allowing the morphology and structural content thereof to be examined. For the specimen, in the case of a tissue sample, a tissue section obtained by thinly sectioning the sample using a microtome and the like may be used, or a whole-mounted tissue or individual may be used, with preference given to a tissue section. The tissue section may be a section of frozen tissue embedded in paraffin or resin. The solid support is not particularly limited, as far as it endures the immobilizing operation, with preference given to one suitable for microscopic examination; examples include glass slides and the like. For sample immobilization, a method known per se may be used; examples include methods using a paraformaldehyde solution, glutaraldehyde solution, osmium tetroxide solution, acetalcohol, methanol, ethanol and the like, or the freezing method, microwave method and the like.

Next, the immobilized sample is preferably treated with a protein degrading enzyme and the like; by this treatment, it is possible to increase the permeability of the peptide of the present invention and the like to be then allowed to act on the immobilized sample into the immobilized sample. Because the treatment inactivates endogenous nucleases, this is also effective in storing double-stranded DNA, which is the target substance. The protein degrading enzyme used for the treatment is not particularly limited; examples include trypsin, pronase, proteinase K and the like, with preference given to proteinase K. The conditions of the treatment can be set as appropriate according to the protein degrading enzyme used; when using, for example, proteinase K, at an enzyme concentration of 1 to 100 µg/mL, the treatment can be achieved in a phosphate buffer solution under 20 to 40° C. conditions for 1 to 60 minutes. When the immobilized sample is a paraffin-embedded section or a resin-embedded section, the sample can be subjected to a protein degrading enzyme treatment after being deparaffinized or deresinated by a conventional method.

Then, by mounting on the immobilized sample a solution containing a peptide of the present invention with a label given thereto in advance and the like, it is possible to contact the peptide and the like and double-stranded DNA. Contact time may be, for example, 10 to 120 minutes under 20 to 40° C. conditions, to which, however, the present invention is not limited. It is also possible to conduct preincubation for one to several tens of minutes with a solution (buffer solution and the like) not containing the peptide and the like only mounted before contact.

As stated above, after contacting the peptide and the like and double-stranded DNA, detection of methylated DNA can be achieved by detecting the label added to the peptide. As the label, for example, a fluorophore, a luminophore, a radioisotope or a hapten or the like can be used. When using a fluorophore or a luminophore, the fluorescence or luminescence thereof can be detected using a fluorescence microscope, a light microscope or a multi-photon laser microscope and the like. It is also possible to process the detected signal by digital imaging to detect methylated DNA three dimensionally. When using a radioisotope, methylated DNA can be detected by measuring the radioactivity thereof using autoradiography, a scintillation counter and the like. In the case of hapten, the detection can be achieved by detecting fluorescence in an immune reaction using a hapten-binding substance (antibody and the like) and a fluorescently labeled antibody that recognizes such a binding substance. The fluorophore used in the fluorescently labeled antibody for recognizing the hapten can be detected using a fluorescence microscope and the like in the same manner as the above.

In another mode of embodiment using a solid phase system, a method of detecting methylated DNA based on enzyme-linked immunosorbent assay (ELISA) may be mentioned.

For example, by immobilizing a peptide of the present invention to a support, adding thereto a test sample to contact the peptide and double-stranded DNA, performing incubation to bind the peptide and the double-stranded DNA methylation region, then washing the same, then adding a labeling antibody that specifically recognizes the double-stranded DNA or a labeled double-stranded DNA-binding peptide to bind the same to the double-stranded DNA remaining on the support, and detecting the label, detection of methylated DNA in the test sample can be achieved. The test sample is not particularly limited, and is preferably a DNA isolation extract from a tissue or cell. The support is exemplified by supports such as synthetic resins such as silicone resin, polystyrene resin, polyacrylamide resin, nylon resin, and polycarbonate resin, as well as glass and the like. These supports can be used in the form of plates and the like; for example, multiwell plates (96-well multiwell plates and the like) and the like can be used. The binding of the peptide of the present invention and the support can be achieved by a method in common use such as chemical bonding or physical adsorption. All these supports may be commercially available products. Before adding the test sample, and after washing the support, a blocking treatment with, for example, bovine serum albumin (BSA), gelatin, albumin and the like can be performed to prevent proteins and the like from nonspecifically binding to the support. When a blocking treatment was performed, the test sample may be added after the support is again washed.

The binding of the peptide and double-stranded DNA is normally achieved in a buffer solution. Useful buffer solutions include, for example, phosphate buffer solutions, Tris buffer solutions, citrate buffer solutions, borate buffer solutions, carbonate buffer solutions and the like. Incubation conditions are not particularly limited, as far as they are in common use; for example, incubation is performed at 4° C. to room temperature for 10 minutes to 15 hours. In the washing after the incubation, the buffer solution is not particularly limited, as far as it does not interfere with the binding of the peptide and double-stranded DNA; for example, a buffer solution containing a surfactant such as Tween 20, Tween 80, or Triton X-100, or the like is used.

After performing the washing, an antibody capable of recognizing the double-stranded DNA, which is previously labeled, or a labeled double-stranded DNA-binding peptide is added. Here, the antibody is not limited to ones that recognize methylated double-stranded DNA; ones that generally recognize double-stranded DNA can be used. The labeled double-stranded DNA-binding peptide may be not only a peptide of the present invention that binds to double-stranded methylated DNA, but also a peptide that binds to unmethylated double-stranded DNA (e.g., publicly known zinc finger peptide). As the label, a radioisotope, an enzyme, a fluorophore, a luminophore, a hapten and the like can be used, and can be added to the antibody or the peptide by a method known per se.

Then, after incubation is performed under appropriate conditions, washing is performed again, and the label remaining on the support is detected. The method of detection can be performed by a method known to those skilled in the art; for example, in the case of labeling with a radioisotope, the label can be detected by liquid scintillation, RIA and the like. In the case of labeling with an enzyme, a substrate is added, and an enzymatic change in the substrate, for example, color development, can be detected using an absorptiometer. Examples of the substrate include 3,3',5,5'-tetramethylbendizine (TMB), 2,2'-azinobis(3-ethylbenzothiazoline-6-sulfonic acid) diammonium salt (ABTS), 1,2-phenylenediamine (ortho-phenylenediamine) and the like. In the case of a fluorophore, the label can be detected using a fluorophotometer.

In the method of detection of the present invention, a step of preparing a control sample and the sample to be detected, and comparing these samples in the presence or absence of DNA methylation, degree or pattern can be included. Based on the results of this comparison, it is possible to test or diagnose a disease on the basis of a DNA methylation abnormality. For testing or diagnostic purposes, it is preferable that DNA methylation be detected quantitatively.

The present invention provides a method of testing DNA methylation abnormalities in a collected sample, comprising (i) a step of contacting a sample collected from a subject animal and the above-described peptide without a metal ion coordinated thereto and a metal ion-supplying compound, or the above-described peptide with a metal ion already coordinated thereto, (ii) a step of measuring the peptide bound to the double-stranded DNA methylation region contained in the sample, and (iii) a step of comparing the measured results for the subject animal in the step (ii) with the measured results for a normal control to determine the presence or absence of a DNA methylation abnormality.

The sample relating to the step (i) is a sample containing double-stranded DNA of the subject animal, and can be obtained in the same manner as the above-described method of detection. Also, contact in the step and the measurement of peptide in the step (ii) can also be achieved in the same manner as the above-described method of detection.

In the step (iii), the measured results obtained in the step (ii) may be compared with the results obtained for a normal control to determine the presence or absence of a DNA methylation abnormality. If the DNA methylation abnormality results in, for example, detection of a signal in a region not methylated in the normal control, or the reverse, or a variation in the level of peptide detected (an increase or decrease is observed), or any difference such as different detection patterns in an examination in a plurality of sites, the subject animal can be judged to be suffering a disease associated with a DNA methylation abnormality, or to be highly likely to have the potential for the onset thereof. Furthermore, the findings obtained by examining the degrees of DNA methylation abnormalities in patients with diseases associated with a wide variety of DNA methylation abnormalities using the method of the present invention for detecting a methylated region in double-stranded DNA and the results obtained using this measuring method may be comprehensively assessed to be helpful in diagnoses (including malignancy and prognosis) of the diseases, therapeutic policies and the like.

Diseases related to DNA methylation abnormalities include, but are not limited to, for example, cancers such as colorectal cancer, lung cancer, mesothelioma, pancreatic cancer, gastric cancer, esophageal cancer, breast cancer, ovarian cancer, prostatic cancer, liver cancer, thyroid cancer, renal cancer, uterine cancer, brain tumor, melanoma, sarcoma, gallbladder cancer, and hematological cancers including multiple myeloma; psychiatric diseases such as schizophrenia, depression, epilepsy, anxiety neurosis, bipolar disorders, mania, alcohol dependence, and drug dependence; lifestyle-related diseases such as diabetes (for example, type 2 diabetes, gestational diabetes, obese diabetes and the like), glucose tolerance insufficiency [IGT (Impaired Glucose Tolerance)], diabetic complications (for example, diabetic retinopathy, diabetic neuropathy, diabetic nephropathy and the like), hyperlipemia (for example, hypertriglyceridemia, hypercholesterolemia, low-HDL-nemia, postprandial hyperlipemia and the like), arteriosclerosis, and gonitis; nervous diseases (for example, Alzheimer's disease, Parkinson's disease, Huntington's disease, amyotrophic lateral sclerosis (ALS), lysosomal storage disease, multiple sclerosis, ischemic neuropathy, spinal cord injury and the like); congenital diseases such as autoimmune diseases (for example, systemic erythematosus, chronic rheumatoid arthritis, ankylosing spondylitis, multiple sclerosis, autoimmune thyroiditis, Hashimoto disease, autoimmune hemolytic anemia, malignant anemia, autoimmune thrombocytopenia, autoimmune cytopenia, myasthenia gravis, scleroderma, polymyositis, secondary Addison's disease, infertility, autoimmune glomerulonephritis, Sjögren's syndrome, vasculitis, autoimmune myelitis, type 1 diabetes, ulcerative colitis, Crohn disease and the like), and circulatory diseases (for example, angina pectoris, hypertension, heart failure, thrombosis and the like) and the like.

In cancer, a wide variety of cancer suppressor genes are inactivated due to epigenetic abnormalities; it is possible to test for DNA methylation abnormalities in cancer suppressor genes in various cancers. In the case of gastric cancer, for example, DNA methylation in a wide variety of genes, including the LOX gene, can be measured; DNA methylation in a wide variety of genes can be measured, including genes such as STAT1, STAT2, STAT5, and 3-OST-2 in the case of colorectal cancer; genes such as KRT8, KRT17, H19, TIMP3, and STAT1 in the case of gallbladder cancer; genes such as 21WAF1, CYR61, NIPSNAP1, CTGF, and DNMT1 in the case of liver cancer. For example, if the DNA methylation of the aforementioned cancer suppressor gene has increased compared with a normal control, the subject animal can be judged to be suffering, or at a high risk of suffering, cancer.

EXAMPLES

The present invention is explained in more detail in the following by referring to Examples, which are not to be construed as limitative.

1. Reagents

The amino acid, genomic DNA and all other reagents used for each test were commercially, available products. The oligoDNA used for the gel shift assay was purchased from GeneDesign, Inc.

2. Synthesis of Peptide

As a test sample, a polypeptide consisting of the following amino acid sequence:

(SEQ ID NO: 12)
RPFMCTWSYCGKRFTRSD<u>X</u>LQRHKRTHTGEKKFACPECPKRFMRSDHLSKHIKTHQNKK was synthesized, and 4 kinds of peptides were prepared according to Table 1. In each peptide, N-terminal was amine, C-terminal was amide, and the phosphorylation site of peptide Y(PO3) (Example 2) and the sulfation site of peptide Y(SO3) (Comparative Example 2) were each p position (position of $R^5$ in the above-mentioned formula (VII)).

TABLE 1

| | amino acid X | name of test sample | reference sequence |
|---|---|---|---|
| Example 1 | tyrosine | peptide Y | SEQ ID NO: 1 |
| Example 2 | phosphotyrosine | peptide Y (PO3) | SEQ ID NO: 2 |
| Comparative Example 1 | phenylalanine | peptide F | SEQ ID NO: 3 |
| Comparative Example 2 | sulfotyrosine | peptide Y (SO3) | SEQ ID NO: 4 |

The peptide consisting of the above-mentioned amino acid sequence has 59 amino acid residues, and the portion corresponding to a metal finger motif is the 5th-27th amino acid sequence from the N-terminal. As for the metal finger motif of each peptide, peptide Y is shown by SEQ ID NO: 5, peptide Y(PO3) is shown by SEQ ID NO: 6, peptide F is shown by SEQ ID NO: 7, and peptide Y (503) is shown by SEQ ID NO: 8. The above-mentioned amino acid sequence is characterized in that the 35th-51st amino acid sequence from the N-terminal thereof is a different metal finger motif (zinc finger).

Each peptide was prepared on an amide resin carrier by an Fmoc solid-phase synthesis and using a peptide automatic synthesizer (Model 433A, APPLIED BIOSYSTEMS). To the obtained solid phase carrier (100 mg) was added trifluoroacetic acid (TFA)/triisopropylsilane (TIS)/1,2-ethanedithiol (EDT)/$H_2O$ (94:1:2.5:2.5 [v/v]) (2 mL), and the mixture was stirred at room temperature for 3 hr and filtered. To the filtrate was added ether (40 mL) to give crude peptide as a white solid. The solid was purified by reversed-phase HPLC (column: Chemcobond 5-ODS-H (10.times.150 mm, Chemco Scientific Co., Ltd.), solvent: 20-50% acetonitrile/0.1°/0 TFA aq.) for 30 min to obtain a given peptide. Each peptide was identified by mass spectrometry using MALDI-TOF MS (Reflex, Bruker Daltonics).

The measured value of peptide Y was 7255.94 ([M+H]⁺, calculated value: 7255.49), the measured value of peptide Y(PO3) was 7335.30 ([M+H]⁺, calculated value: 7335.48), the measured value of peptide F was 7239.08 ([M+H]⁺, calculated value: 7239.49), and the measured value of peptide Y(SO3) was 7334.9([M+H]⁺, calculated value: 7334.55). An excess amount of $ZnCl_2$ was added to each peptide thus obtained to give a zinc finger peptide.

3. Structural Confirmation of Peptide

To examine whether 4 kinds of peptides prepared as mentioned above form a folding structure by binding with a metal ion, CD spectrum thereof was measured. As a method therefor, the concentration of peptide Y was adjusted to 20 µM, the concentration of peptide Y(PO3) was adjusted to 18 µM, the concentration of peptide F was adjusted to 18 µM, and the concentration of peptide Y (SO3) was adjusted to 19 µM with a dilution solution (10 mM Tris-HCl buffer (pH 7.5), 50 mM NaCl, 0.1 mM TCEP, 60 µM $ZnCl_2$), and the measurement was performed using a cell with optical path length 1 mm, under nitrogen at 4° C. For the measurement, a circular dichroism spectrometer (JASCO, J-720) was used, and baseline amendment and data processing by the following calculation formula (I) were performed using the software attached to the apparatus to give each CD spectrum. The results are shown in FIG. 1.

[equation 1]

$$[\theta] = \theta/lcn \qquad (1)$$

[θ]: mean residue ellipticity (deg cm² dmol⁻¹)
θ: ellipticity (deg)
l: optical path length (cm)
c: peptide concentration (M)
n: number of constituent residues From the results of FIG. 1, negative peaks near 208 nm and 222 nm and a positive peak near 190 nm were detected in all the peptides, which confirmed formation of α helix structure therein.

4. Preparation of Labeled Target DNA

In the oligonucleotides consisting of the following nucleotide sequences:

```
                                    (SEQ ID NO: 9)
5'- GGGGMGGGGCC -3'  (G chain)

(SEQ ID NO: 10)
5'- GGCCCMGCCCC -3'  (C chain),
``` the 5'-terminal of the G chain was ³²P labeled with [γ-³²P] ATP and T4 polynucleotide kinase, and unlabeled C chain was added to allow annealing, whereby a ³²P-labeled target methylated DNA was obtained. In the sequence, M shows methylcytosine wherein the 5-position carbon is methylated.

In the oligonucleotide consisting of the following nucleotide sequence:

```
                                    (SEQ ID NO: 11)
5'- GGGGCGGGGCC -3',
``` the 5'-terminal was similarly ³²P labeled, and complementary oligonucleotide (unlabeled) with the same base number was added to give a ³²P-labeled target unmethylated DNA.

5. Synthesis of Fluorescence-Labeled Peptide (Peptide Y(PO3))

Fmoc-6-aminohexanoic acid (12.4 mg, 35 mmol), benzotriazol-1-yl-oxy-tris-pyrrolidino-phosphonium hexafluorophosphate (PyBOP) (18.2 mg, 35 mmol), and 1-hydroxybenzotriazole (HOBt) (4.7 mg, 35 mmol) were dissolved in N,N-dimethylformamide (DMF) (0.5 mL), thereto was added N,N-diisopropylethylamine (DIEA) (12.2 mL, 70 mmol), and the mixture was added to a peptide (peptide Y(PO3)) (100 mg, 7 mmol) on a carrier, which was prepared by a peptide automatic synthesizer. After stirring at room temperature for 1 hr, the reaction solution was discarded, and the carrier was washed with DMF, methanol and ether, and dried under reduced pressure. To the obtained carrier was added 20% piperidine/DMF (1 mL) and, after stirring for 2 min, the solution was discarded. This operation was repeated 5 times, and the carrier was washed with DMF, methanol and ether, and dried under reduced pressure. 5-(and-6)-Carboxyfluorescein succinimidyl ester (6.6 mg (FAM SE, 14 mmol) and HOBt (1.9 mg, 14 mmol) were dissolved in DMF (0.5 mL), thereto was added DIEA (4.9 mL, 28 mmol) and the mixture was added to the carrier. After stirring at room temperature in a dark place for 12 hr, the reaction solution was discarded, and the carrier was washed with DMF, methanol and ether, and dried under reduced pressure. The peptide on the obtained carrier was cleaved out from the carrier according to the above-described method, and subjected to deprotection and purification to afford a given peptide. The peptide was identified by MALDI-TOF MS (Reflex, Bruker Daltonics) in the same manner as above. The measured value was 7805.64 ([M+H]⁺, calculated value: 7806.93).

Test 1. Gel Shift Assay

³²P-labeled target (methylated or unmethylated) DNA (500 cpm, ~50 µM), the above-mentioned synthetic peptide (0-7.5 µM), 20 mM Tris-HCl (pH 8.0), 100 mM NaCl, 100 µM $ZnCl_2$, 1 mM Tris (2-carboxyethyl)-phosphine (TCEP), 0.05% Nonidet P-40, 5% glycerol, 40 ng/µL bovine serum albumin (BSA), and 100 ng/µL poly(dI-dC) were stood at 4° C. for 30 min to allow reaction, and the reaction solution was electrophoresed on 12% polyacrylamide gel (1× Tris-borate (TB) buffer). The results are shown in FIG. 2.

Figure 2:
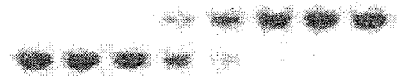
FIG. 2 shows the results of a gel shift assay examining the bindability of the 4 kinds of peptides and methylated DNA. (1) shows the results for peptide Y (Example 1), (2) for peptide Y(PO3) (Example 2), (3) for peptide F (Comparative Example 1), and (4) for peptide Y(SO3) (Comparative Example 2); for each peptide, the left panel shows the result of gel shift assay for binding to methylated DNA, and the right panel shows the result of gel shift assay for binding to unmethylated DNA. The upper bands indicated on the gel show conjugates of each peptide and DNA, and the lower bands show bands of DNA not bound to each peptide.
Figure 2:
Figure 2:
Figure 2:
Figure 2:
Figure 2:
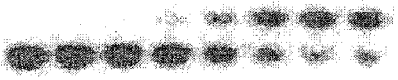
Figure 2:
Figure 2:

As shown in FIG. 2, it was found that peptide Y (Example 1) began to bind to methylated DNA at a concentration of 0.25 µM, and that the bindability thereof increased as the concentration rose. Although binding to unmethylated DNA began to be observed at a concentration of 0.5 µM, this peptide was found to be less bindable than to methylated DNA. Regarding peptide Y(PO3) (Example 2), the bindability to methylated DNA increased as the concentration rose, with the binding thereof beginning to be observed at 0.1 µM. It was found that this peptide little bound to unmethylated DNA. In contrast, peptide F (Comparative Example 1) did not exhibit a difference in the is status of binding between the methylated DNA and unmethylated DNA. As for peptide Y(SO3) (Comparative Example 2), almost no binding was observed for both methylated DNA and unmethylated DNA despite the formation of α helix structure as shown in FIG. 1.

These bands obtained on the gel were quantified using Image Gauge software (FUJIFILM Corporation, ver. 4.01). The ratio of DNA bound to the peptide ([bound]/[bound]+[free]) was calculated from the band intensity at each peptide concentration; using this and the concentration of the peptide, the dissociation constant between the peptide and the DNA was calculated from the calculation equation (2) below. The results are shown in Table 2.

[equation 2]

$$F = [P]/([P] + Kd) \qquad (2)$$

(F: ratio of DNA bound to peptide, [P]: total peptide concentration, Kd: dissociation constant)

TABLE 2

| Name of test sample | | Kd (μM) | |
|---|---|---|---|
| | | Methylated DNA | Unmethylated DNA |
| Example 1 | Peptide Y | 0.718 ± 0.113 | 1.39 ± 0.234 |
| Example 2 | Peptide Y (PO3) | 0.698 ± 0.0513 | 8.74 ± 0.545 |
| Comparative Example 1 | Peptide F | 5.58 ± 0.439 | 2.10 ± 0.169 |
| Comparative Example 2 | Peptide Y (SO3) | 26.4 ± 1.83 | 20.6 ± 0.322 |

As shown in Table 2, for both peptide Y (Example 1) and peptide Y(PO3) (Example 2), the dissociation constant in methylated DNA was less than 1.0, demonstrating that the bindability was extremely high. The dissociation constant in unmethylated DNA exceeded 1.0 for both peptides, demonstrating that both bound specifically to the methylated DNA. Furthermore, the ratio of the dissociation constant of methylated DNA to unmethylated DNA was calculated to be about 1.94 (1.39/0.718) for peptide Y and about 12.5 (8.74/0.698) for peptide Y(PO3). This demonstrated that peptide Y(PO3) bound more specifically to methylated DNA than peptide Y. Both peptide F (Comparative Example 1) and peptide Y(SO3) (Comparative Example 2) were low in bindability to methylated DNA and unmethylated DNA, and did not exhibit specificity for binding to methylated DNA.

Test 2. Measurement of Fluorescence Polarization

Methylated genomic DNA (Jurkat Genomic DNA) and unmethylated genomic DNA (5-Azadc treated Jurkat Genomic DNA) were each subjected to ethanol precipitation, and dissolved in 10 mM Tris-HCl (pH 8). Each genomic DNA was added to a fluorescence-labeled peptide (0.05 pH), 20 mM Tris-HCl (pH 8), 100 mM NaCl, 20 mM $ZnCl_2$, 1 mM TCEP, 0.05% Nonidet P-40, and the mixture was stirred. This was stood at 25° C. for 10 min to allow reaction, and fluorescence polarization was measured by a plate reader (Mithras LB 940, Berthold). The concentration (ng/μL) of each genomic DNA was 0.4, 0.8, 1.2, 1.6, 2.0, 2.4, 2.8, 3.2, 3.6, 4.0 and the value calculated by the plate reader was used for polarization. The results are shown in FIG. 3.

Figure 3:
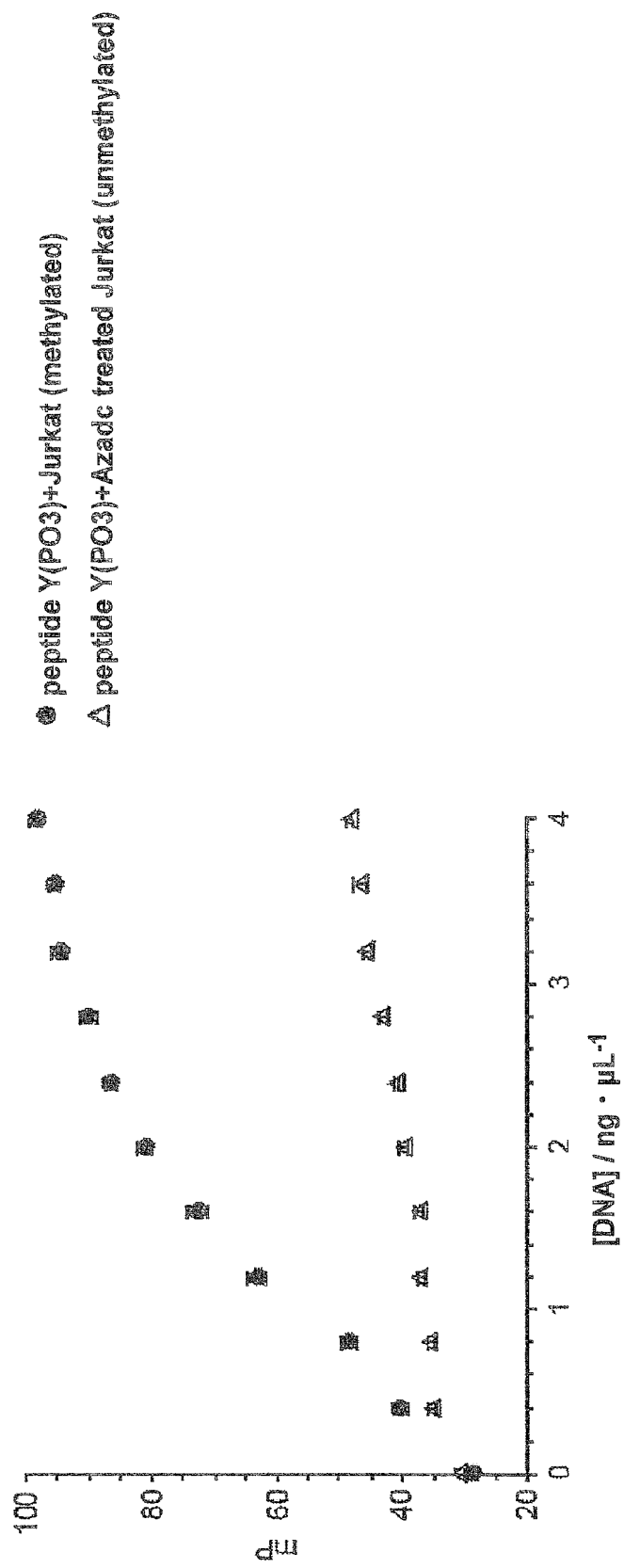
FIG. 3 shows the results of a measurement of fluorescence polarization in the binding of peptide Y(PO3) (Example 2) and methylated DNA. The vertical axis indicates the magnitude of polarization (mP), and the horizontal axis indicates the concentration (ng/μL) of DNA. The circles indicate fluorescence polarization in the binding of peptide Y(PO3) and methylated DNA, and the triangles indicate fluorescence polarization in the binding of peptide Y(PO3) and unmethylated DNA.

As shown in FIG. 3, for the reaction product of a fluorescence-labeled peptide and methylated genomic DNA (Jurkat), the measured value of fluorescence polarization increased depending on the concentration of DNA added. In contrast, for the reaction product with unmethylated genomic DNA (5-Azadc treated Jurkat), the measured value of fluorescence polarization remained almost unchanged even when DNA was added. These results demonstrated that a fluorescence-labeled peptide (peptide Y(PO3)) bound to methylated double-stranded DNA at the genome level as well, showing that the binding of the peptide of the present invention and the double-stranded DNA methylation region possesses quantitative analyzability.

INDUSTRIAL APPLICABILITY

According to the present invention, it is possible to detect and quantify a DNA methylation region in a short time, with saved labor, and non-specifically for nucleotide sequences, making it possible to provide a diagnostic or testing tool useful in a wide variety of diseases caused by DNA methylation abnormalities, such as cancer, differentiation abnormalities, schizophrenia, and diabetes. The peptide of the present invention can also serve as a tool for identification for transplanted organs, playing an important role in regenerative medicine as well.

This application is based on patent application No. 2009-239657 (filing date: Oct. 16, 2009) filed in Japan, the contents of which are encompassed in full herein.

The invention claimed is:

1. A method of detecting a methylated region of a double stranded DNA, comprising the following steps:
   (i) contacting a double stranded DNA with either
      (a) a peptide comprising an amino acid sequence selected from SEQ ID NOs: 1-8, and a metal ion supply compound, or
      (b) a peptide comprising an amino acid sequence selected from SEQ ID NOs: 1-8, wherein a metal ion is coordinately bound to the peptide; and
   (ii) detecting the peptide bound to a methylated region of the double stranded DNA.

2. The detection method according to claim 1, wherein the metal ion supply compound is a compound comprising one or more metal atoms selected from the group consisting of zinc, magnesium, cadmium, manganese, calcium, cobalt and iron.

3. A method to determine the presence or absence of a DNA methylation abnormality in a subject animal, comprising the following steps (i)-(iii):
   (i) contacting a sample obtained from a subject animal with either
      (a) a peptide comprising an amino acid sequence selected from SEQ ID NOs: 1-8, and a metal ion supply compound, or
      (b) a peptide comprising an amino acid sequence selected from SEQ ID NOs: 1-8, wherein a metal ion is coordinately bound to the peptide;
   (ii) measuring the peptide bound to a methylated region of a double stranded DNA contained in the sample; and
   (iii) comparing the measurement results obtained for the subject animal in step (ii) with those of a normal control sample.

4. The method according to claim 3, wherein the metal ion supply compound is a compound comprising one or more metal atoms selected from the group consisting of zinc, magnesium, cadmium, manganese, calcium, cobalt and iron.

5. The method according to claim 3, wherein the DNA methylation abnormality is caused by a disease related to a DNA methylation abnormality.

6. The method according to claim 5, wherein the disease related to the DNA methylation abnormality is a cancer, a psychiatric disease, diabetes, hyperlipidemia, arteriosclerosis, a neurological disease, an autoimmune disease, angina pectoris, hypertension, heart failure, or thrombosis.

* * * * *

SEQUENCE LISTING

<160> NUMBER OF SEQ ID NOS: 12

<210> SEQ ID NO 1
<211> LENGTH: 59
<212> TYPE: PRT
<213> ORGANISM: Artificial Sequence
<220> FEATURE:
<223> OTHER INFORMATION: Synthetically generated polypeptide

<400> SEQUENCE: 1

Arg Pro Phe Met Cys Thr Trp Ser Tyr Cys Gly Lys Arg Phe Thr Arg
1               5                   10                  15

Ser Asp Tyr Leu Gln Arg His Lys Arg Thr His Thr Gly Glu Lys Lys
            20                  25                  30

Phe Ala Cys Pro Glu Cys Pro Lys Arg Phe Met Arg Ser Asp His Leu
        35                  40                  45

Ser Lys His Ile Lys Thr His Gln Asn Lys Lys
    50                  55

<210> SEQ ID NO 2
<211> LENGTH: 59
<212> TYPE: PRT
<213> ORGANISM: Artificial Sequence
<220> FEATURE:
<223> OTHER INFORMATION: Synthetically generated polypeptide

```
<220> FEATURE:
<221> NAME/KEY: MOD_RES
<222> LOCATION: (19)..(19)
<223> OTHER INFORMATION: PHOSPHORYLATION

<400> SEQUENCE: 2

Arg Pro Phe Met Cys Thr Trp Ser Tyr Cys Gly Lys Arg Phe Thr Arg
1               5                   10                  15

Ser Asp Tyr Leu Gln Arg His Lys Arg Thr His Thr Gly Glu Lys Lys
                20                  25                  30

Phe Ala Cys Pro Glu Cys Pro Lys Arg Phe Met Arg Ser Asp His Leu
            35                  40                  45

Ser Lys His Ile Lys Thr His Gln Asn Lys Lys
        50                  55

<210> SEQ ID NO 3
<211> LENGTH: 59
<212> TYPE: PRT
<213> ORGANISM: Artificial Sequence
<220> FEATURE:
<223> OTHER INFORMATION: Synthetically generated polypeptide

<400> SEQUENCE: 3

Arg Pro Phe Met Cys Thr Trp Ser Tyr Cys Gly Lys Arg Phe Thr Arg
1               5                   10                  15

Ser Asp Phe Leu Gln Arg His Lys Arg Thr His Thr Gly Glu Lys Lys
                20                  25                  30

Phe Ala Cys Pro Glu Cys Pro Lys Arg Phe Met Arg Ser Asp His Leu
            35                  40                  45

Ser Lys His Ile Lys Thr His Gln Asn Lys Lys
        50                  55

<210> SEQ ID NO 4
<211> LENGTH: 59
<212> TYPE: PRT
<213> ORGANISM: Artificial Sequence
<220> FEATURE:
<223> OTHER INFORMATION: Synthetically generated polypeptide
<220> FEATURE:
<221> NAME/KEY: MOD_RES
<222> LOCATION: (19)..(19)
<223> OTHER INFORMATION: SULFATATION

<400> SEQUENCE: 4

Arg Pro Phe Met Cys Thr Trp Ser Tyr Cys Gly Lys Arg Phe Thr Arg
1               5                   10                  15

Ser Asp Tyr Leu Gln Arg His Lys Arg Thr His Thr Gly Glu Lys Lys
                20                  25                  30

Phe Ala Cys Pro Glu Cys Pro Lys Arg Phe Met Arg Ser Asp His Leu
            35                  40                  45

Ser Lys His Ile Lys Thr His Gln Asn Lys Lys
        50                  55

<210> SEQ ID NO 5
<211> LENGTH: 23
<212> TYPE: PRT
<213> ORGANISM: Artificial Sequence
<220> FEATURE:
<223> OTHER INFORMATION: Synthetically generated polypeptide
```

```
<400> SEQUENCE: 5

Cys Thr Trp Ser Tyr Cys Gly Lys Arg Phe Thr Arg Ser Asp Tyr Leu
1               5                   10                  15

Gln Arg His Lys Arg Thr His
            20

<210> SEQ ID NO 6
<211> LENGTH: 23
<212> TYPE: PRT
<213> ORGANISM: Artificial Sequence
<220> FEATURE:
<223> OTHER INFORMATION: Synthetically generated polypeptide
<220> FEATURE:
<221> NAME/KEY: MOD_RES
<222> LOCATION: (15)..(15)
<223> OTHER INFORMATION: PHOSPHORYLATION

<400> SEQUENCE: 6

Cys Thr Trp Ser Tyr Cys Gly Lys Arg Phe Thr Arg Ser Asp Tyr Leu
1               5                   10                  15

Gln Arg His Lys Arg Thr His
            20

<210> SEQ ID NO 7
<211> LENGTH: 23
<212> TYPE: PRT
<213> ORGANISM: Artificial Sequence
<220> FEATURE:
<223> OTHER INFORMATION: Synthetically generated polypeptide

<400> SEQUENCE: 7

Cys Thr Trp Ser Tyr Cys Gly Lys Arg Phe Thr Arg Ser Asp Phe Leu
1               5                   10                  15

Gln Arg His Lys Arg Thr His
            20

<210> SEQ ID NO 8
<211> LENGTH: 23
<212> TYPE: PRT
<213> ORGANISM: Artificial Sequence
<220> FEATURE:
<223> OTHER INFORMATION: Synthetically generated polypeptide
<220> FEATURE:
<221> NAME/KEY: MOD_RES
<222> LOCATION: (15)..(15)
<223> OTHER INFORMATION: SULFATATION

<400> SEQUENCE: 8

Cys Thr Trp Ser Tyr Cys Gly Lys Arg Phe Thr Arg Ser Asp Tyr Leu
1               5                   10                  15

Gln Arg His Lys Arg Thr His
            20

<210> SEQ ID NO 9
<211> LENGTH: 11
<212> TYPE: DNA
<213> ORGANISM: Artificial Sequence
<220> FEATURE:
<223> OTHER INFORMATION: Synthetically generated oligonucleotide
<220> FEATURE:
<221> NAME/KEY: modified_base
<222> LOCATION: (5)..(5)
<223> OTHER INFORMATION: m5c

<400> SEQUENCE: 9
ggggcggggc c                                                                11
```

```
<210> SEQ ID NO 10
<211> LENGTH: 11
<212> TYPE: DNA
<213> ORGANISM: Artificial Sequence
<220> FEATURE:
<223> OTHER INFORMATION: Synthetically generated oligonucleotide
<220> FEATURE:
<221> NAME/KEY: modified_base
<222> LOCATION: (6)..(6)
<223> OTHER INFORMATION: m5c

<400> SEQUENCE: 10
ggccccgccc c                                                              11

<210> SEQ ID NO 11
<211> LENGTH: 11
<212> TYPE: DNA
<213> ORGANISM: Artificial Sequence
<220> FEATURE:
<223> OTHER INFORMATION: Synthetically generated oligonucleotide

<400> SEQUENCE: 11
ggggcggggc c                                                              11

<210> SEQ ID NO 12
<211> LENGTH: 59
<212> TYPE: PRT
<213> ORGANISM: Artificial Sequence
<220> FEATURE:
<223> OTHER INFORMATION: Synthetically generated polypeptide
<220> FEATURE:
<221> NAME/KEY: misc_feature
<222> LOCATION: (19)..(19)
<223> OTHER INFORMATION: Xaa can be any naturally occurring amino acid

<400> SEQUENCE: 12

Arg Pro Phe Met Cys Thr Trp Ser Tyr Cys Gly Lys Arg Phe Thr Arg
1               5                   10                  15

Ser Asp Xaa Leu Gln Arg His Lys Arg Thr His Thr Gly Glu Lys Lys
            20                  25                  30

Phe Ala Cys Pro Glu Cys Pro Lys Arg Phe Met Arg Ser Asp His Leu
        35                  40                  45

Ser Lys His Ile Lys Thr His Gln Asn Lys Lys
    50                  55
```